US005840674A

United States Patent [19]
Yatvin et al.

[11] Patent Number: 5,840,674
[45] Date of Patent: Nov. 24, 1998

[54] COVALENT MICROPARTICLE-DRUG CONJUGATES FOR BIOLOGICAL TARGETING

[75] Inventors: Milton B. Yatvin, Portland, Oreg.; Michael H. B. Stowell, Padadena, Calif.; Vincent S. Gallicchio, Lexington, Ky.; Michael J. Meredith, Lake Oswego, Oreg.

[73] Assignee: Oregon Health Sciences University, Portland, Oreg.

[21] Appl. No.: 691,891

[22] Filed: Aug. 1, 1996

Related U.S. Application Data

[63] Continuation of Ser. No. 441,770, May 16, 1995, Pat. No. 5,543,391, and Ser. No. 246,941, May 19, 1994, Pat. No. 5,543,390, which is a continuation-in-part of Ser. No. 142, 771, Oct. 26, 1993, Pat. No. 5,543,389, which is a continuation-in-part of Ser. No. 911,209, Jul. 9, 1992, Pat. No. 5,256,641, which is a continuation-in-part of Ser. No. 607, 982, Nov. 1, 1990, Pat. No. 5,149,794.

[51] Int. Cl.$^6$ ............................ A01N 37/18; A01N 57/26
[52] U.S. Cl. ............................ 514/2; 514/78; 424/450; 536/21; 536/51; 530/300; 530/331; 530/329
[58] Field of Search ........................ 514/2, 78; 424/450; 536/21, 51; 530/300, 331, 329

[56] References Cited

U.S. PATENT DOCUMENTS

| | | | |
|---|---|---|---|
| 4,780,455 | 10/1988 | Liberman et al. | 514/77 |
| 4,793,986 | 12/1988 | Serino et al. | 424/1.53 |
| 4,847,240 | 7/1989 | Ryser et al. | 514/12 |
| 5,053,394 | 10/1991 | Ellestad et al. | 530/391.9 |
| 5,258,453 | 11/1993 | Kopecek et al. | 525/54.1 |

FOREIGN PATENT DOCUMENTS

| | | | |
|---|---|---|---|
| 1094844 | 4/1983 | European Pat. Off. | |
| 3012233 | 12/1983 | European Pat. Off. | |
| 1057469 | 8/1988 | European Pat. Off. | |
| 350287 | 1/1990 | European Pat. Off. | C07A 19/073 |
| 8900166 | 11/1989 | WIPO. | |
| 8902909 | 1/1990 | WIPO. | |
| 9001002 | 9/1990 | WIPO. | |
| 9004087 | 2/1991 | WIPO. | |
| 9102691 | 10/1991 | WIPO. | |
| 9401138 | 1/1994 | WIPO | A61K 47/48 |
| 9425616 | 11/1994 | WIPO | C12P 21/00 |

OTHER PUBLICATIONS

Afzelius et al., *Biochim. Biophys. Acta* 979: 231–238 (1989).
Alvarez–Doninquez et al., "Role of Complement Component C1q in Phagocytosis of *Listeria monocytogenes* by Murine Macrophage–Like Cell Lines,"*Infect. Immun.* 61: 3664–3672 (1993).
Anderson et al., *J Am. Chem. Soc.* 85: 3039 (1963).
Ashborn et al., "Anti–HIV Activity of CD4–*Pseudomonas* Exotoxin on Infected Primary Human Lympocytes and Monocyte/Macrophages," *J Infect. Dis.* 163: 703–709 (1991).
Baer, *Can. J Biochem. Phys.* 34: 288–304 (1955).
Bai and Amidon, "Structural Specificity of Mucosal–Cell Transport and Metabolism of Peptide Drugs: Implications for Oral Peptide Drug Delivery," *Pharm. Res.* 9: 969–978 (1992).
Bai et al., "Utilization of Peptide Carrier System to Improve Intestinal Absorption: Targeting Prolidase as a Prodrug–Converting Enzyme," *J Pharm. Sci.* 81: 113–116 (1992).
Baroni et al., "Expression of HIV in Lymph Node Cells of LAS Patients: Immunohistology, In Situ Hybridization, and Identification of Target Cells," *Am. J Pathol.* 133: 498–506 (1988).
Berdel et al., *Lipids* 22: 943–946 (1987).
Bickel et al., "Pharmacologic effects in vivo in brain by vector–mediated peptide drug delivery," *Proc. Natl. Acad. Sci. USA* 90: 2618–2622 (1993).

(List continued on next page.)

*Primary Examiner*—John W. Rollins
*Attorney, Agent, or Firm*—McDonnell, Boehnen, Hulbert & Berghoff

[57] ABSTRACT

This invention provides novel methods and reagents for specifically delivering biologically active compounds to phagocytic mammalian cells. The invention also relates to specific uptake of such biologically active compounds by phagocytic cells and delivery of such compounds to specific sites intracellularly. The invention specifically relates to methods of facilitating the entry of antiviral and antimicrobial drugs and other agents into phagocytic cells and for targeting such compounds to specific organelles within the cell. The invention specifically provides compositions of matter and pharmaceutical embodiments of such compositions comprising conjugates of such antimicrobial drugs and agents covalently linked to particulate carriers generally termed microparticles. In particular embodiments, the antimicrobial drug is covalently linked to a microparticle via an organic linker molecule which is the target of a microorganism-specific protein having enzymatic activity. Thus, the invention provides cell targeting of drugs wherein the targeted drug is only released in cells infected with a particular microorganism. Alternative embodiments of such specific drug delivery compositions also contain polar lipid carrier molecules effective in achieving intracellular organelle targeting in infected phagocytic mammalian cells. Particular embodiments of such conjugates comprise antimicrobial drugs or agents covalently linked both to a microparticle via an organic linker molecule and to a polar lipid compound, to facilitate targeting of such drugs or agents to particular subcellular organelles within the cell. Also provided are porous microparticles impregnated with antiviral and antimicrobial drugs and agents wherein the surface or outside extent of the microparticle is covered with a degradable coating that is specifically degraded within an infected phagocytic mammalian cell. Also provided are nonporous microparticles coated with an antiviral or antimicrobial drug and further coated wherein the surface or outside extent of the microparticle is covered with a degradable coating that is specifically degraded within an infected phagocytic mammalian cell. Methods of inhibiting, attenuating, arresting, combating and overcoming microbial infection of phagocytic mammalian cells in vivo and in vitro are also provided.

25 Claims, 13 Drawing Sheets

OTHER PUBLICATIONS

Blakey, "Drug Targeting with Monoclonal Antibodies," *Acta Oncol.* 31: 91–97 (1992).

Blight et al., "Detection of hepatitis C virus RNA by in situ hybridization," *Liver* 12: 286–289 (1992).

Blum et al., "Bloood clearance and organ deposition of intravenously administered colloidal particles: the effects of particle size, nature and shape," *Int. J Pharm.* 12: 135–146 (1982).

Boman et al., "Cell–free immunity in Cecropia: A model system for antibacterial proteins," *Eur. J. Biochem.* 201: 23–31 (1990).

Borissova et al., "Biodegradable Microspheres. 17. Lysosomal Degradation of Primaquine–Peptide Spacer Arms," *Journal of Pharmaceutical Sciences,* vol. 84, No. 2, Feb. 1995, pp. 256–262.

Brewster et al., "Improved Delivery through Biological Membranes XXXI: Solubilization and Stabilization of an Estradiol Chemical Delivery System by Modified β–Cyclodextrins," *J Pharm. Sci.* 77: 981–985 (1985).

Bromberg et al., "Detection of *Borditella pertussis* Associated with the Alveolar Macrophages of Children with Human Immunodeficiency Virus Infection," *Infect. Immun.* 59: 4715–4719 (1991).

Brown & Silvius, *Biochim. Biophys. Acta* 1023: 341–351 (1990).

Buchmeier and Heffron, "Induction of Salmonella Stress Proteins upon Infection of Macrophages," *Science* 248: 730–732 (1990).

Chang, "*Leishmania donovani:* Promastigote–Macrophage Surface Interactions in Vitro," *Exp. Parisitol.* 48: 175–189 (1979).

Clarke et al., "Detection of HIV–1 in human lung macrophages using the polymerase chaine reaction," *AIDS* 4: 1133–1136 (1990).

Comiskey & Heath, *Biochim. Biophys. Acta* 1024: 307–317 (1990).

Cordier et al., "In vivo Activation of Alveolar Macrophages in Ovine Lentivirus Infection," *Clin. Immunol. Immunopathol.* 55: 355–367 (1990).

Couveur and Puisieux, "Nano–and microparticles for the delivery of polypeptides and proteins," *Adv. Drug Deliv. Rev.* 10: 141–162 (1993).

Debs et al., *Biochim. Biophys. Acta* 901: 183–190 (1987).

Dreyer et al., *Proc. Natl. Acad. Sci. USA* 86: 9752–9756 (1989).

Duncan, "Drug–polymer conjugates: potential for improved chemotherapy," *Anticancer Drugs* 3: 175–210 (1992).

Embretson et al., "Massive covert infection of helper T lymphocytes and macrophages by HIV during the incubation period of AIDS," *Nature* 362: 359–361 (1993).

Faulk et al., "Transferrin–Adriamycin Conjugates which Inhibit Tumor Cell Proliferation without Interaction with DNA Inhibit Plasma Membrane Oxidoreductase and Proton Release in K562 Cells," *Biochem. Int.* 25: 815–822 (1991).

Franssen et al., "Low Molecular Weight Proteins as Carrier for Renal Drug Targeting: Preparation of Drug–Protein Conjugates and Drug–Spacer Derivatives and Their Catabolism in Renal Cortex Homogenates and Lysosomal Lysates," *J Med. Chem.* 35: 1246–1259 (1992).

Frehel et al., Intramacrophage Growth of *Mycobacterium avium* during Infection of Mice, *Infect. Immun.* 59: 2207–2214 (1991).

Friedman et al., "Uptake and Intracellular Survival of *Bordatella pertussis* in Human Macrophages," *Infect. Immun.* 60: 4578–4585 (1992).

Gaspar et al., "Drug targeting with polyalkylcyanoacrylate nanoparticles: in vitro activity of primaquine–loaded nanoparticles against intracellular *Leishmania donovani,*" *Ann. Trop. Med. Parasitol.* 86: 41–49 (1992).

Gendelman et al., "Slow, persistent replication of lentiviruses: Role of tissue macrophages and macrophage precursors in bone marrow," *Proc. Natl. Acad. Sci. USA* 82: 7086–7090 (1985).

Groisman et al., "Resistance to host antimicrobial peptides is necessary for *Salmonella* virulence," *Proc. Natl. Acad. Sci. USA* 89: 11939–11943 (1992).

Halstead et al., "Dengue Viruses and Mononuclear Phagocytes: I. Infection Enhancement by Non–Neutralizing Antibody," *J Exp. Med.* 146: 201–217 (1977).

Hashimoto et al., *Biochim. Biophys. Acta* 816: 163–168 (1985).

Hashimoto et al., *Biochim. Biophys. Acta* 816: 169–178 (1985).

Heath and Martin, *Chem. Phys. Lipids* 40: 347–358 (1986).

Heath et al., *Biochim. Biophys. Acta* 862: 72–80 (1986).

Heath, Methods *in Enzymol.* 149: 111–119.

Heinrich et al., "In–vivo Release of a GnRH Agonist from a Slow–release Poly(lactide–glycolide) Copolymer Preparation: Comparison in Rat, Rabbit and Guniea–Pig," *J Pharm. Pharmacol.* 43: 762–765 (1991).

Horwitz and Maxfield, "*Legionella pneumphila* Inhibits Acidification of its Phagosome in Human Monocytes," *J Cell Biol.* 99: 1936–1943 (1984).

Horwitz, "Interactions between Macrophages and *Legionella pneumophila*," *Curr. Top. Microbiol Immunol.* 181: 265–282 (1992).

Horwitz, "The Legionnaires' Disease Bacterium (*Legionella pneumophila*) Inhibits Phagosome–Lysosome Fusion in Human Monocytes," *J Exp. Med.* 158: 2108–2126 (1983).

Hostetler et al., *J Biol. Chem.* 265: 6112–6117 (1990).

Hunter et al., "Vesicular Systems (Niosomes and Liposomes) for Delivery of Sodium Stibogluconate in Experimental Murine Visceral Leishmaniasis," *J Pharm. Phamacol.* 40: 161–165 (1988).

Jacobson et al., *FEBS Lett.* 225: 97–102 (1987).

Jones and Hirsch, "the Interaction between Tosoplasma gondii and Mammalian Cells," *J Exp. Med.* 136: 1173–1194 (1972).

Kanno et al., "Aleutian Mink Disease Parvovirus Infection of Mink Peritoneal Macrophages and Human Macrophage Cell Lines," *J Virol.* 67: 2075–2082 (1993).

Kanno et al., "Identification of Aleutian Mink Disease Parvovirus Transcripts in Macrophages of Infected Adult Mink," *J Virol.* 66: 5305–5312 (1992).

King et al., "In Vivo Selection of Lymphocyte–Tropic and Macrophage–Tropic Variants of Lymphocytic Chorimeningitis Virus during Persistent Infection," *J. Virol.* 64: 5611–5616 (1990).

Kinsky & Loeder, *Biochim. Biophys. Acta* 921: 96–103 (1987).

Kinsky et al., *Biochim. Biophys. Acta* 885: 129–135 (1986).

Kinsky et al., *Biochim. Biophys. Acta* 917: 211–218 (1987).

Kishimoto, *Chem. Phys. Lipids* 15: 33–36 (1975).

Koenig et al., "Detection of AIDS Virus in Macrophages in Brain Tissue from AIDS Patients with Encephalopathy," *Science* 233: 1089–1093 (1986).

Kondo et al., "Latent human herpesvirus 6 infection of human monocytes/macrophages," *J Gen. Virol.* 72: 1401–1408 (1991).

Koval & Pagano, *J. Cell Biol.* 108: 2169–2181 (1989).

Krowka et al., *J Immunol.* 144: 2535–2540 (1990).

Kung and Redemann, *Biochim. Biophys. Acta* 862: 435–439 (1986).

Larsen et al., "Stability of ketoprofen–dextran ester prodrugs in homogenates of various segments of the pig GI tract," *Acta Pharm. Nord.* 3: 41–44 (1991).

Lee et al., "Antibacterial peptides from pig intestines: Isolation of a mamalian cecropin," *Proc. Natl. Acad. Sci. USA* 86: 9159–9162 (1989).

Lehrer et al., "Defensins: Endogenous Antibiotic Peptides of Animal Cells," *Cell* 64: 229–230 (1991).

Lin et al., "Preparation of Enteric–Coated Microspheres of myplasma hyopneumoniae vaccine with cellulose acetate; (ii) effect of temperature and ph on the stability and release behaviour of microspheres," *Journal of Microencapsulation,* vol. 8, No. 4: 537–545 (1991).
Loughery et al., *J Immunol. Methods* 132: 25–35 (1990).
MacDonald, *J Biol. Chem.* 265: 13533–13539 (1990).
Maciejewski et al., "Infection of Mononucleated Phagocytes with Human Cytomegalovirus," *Virol.* 195: 327–336 (1993).
Matsura et al., *J Chem. Soc. Chem. Comm.* xx: 451–459 (1976).
Mauel et al., "Quantitative Release of Live Micro–organisms from Infected Macrophages by Sodium Dodecyl Sulfate," *Nature New Biol.* 244: 93–94 (1973).
Mauel, "Macrophage–Parasite Interactions in Leishmania Infections," *J Leukocyte Biol.* 47: 187–193 (1990).
McEntee et al., "Rhesus monkey macrophages infected with simian immunodeficiency virus cause rapid lysis of CD4–bearing lymphocytes," *J Gen. Virol.* 72: 317–324 (1991).
Meltzer and Gendelman, "Mononuclear Phagocytes as Targets, Tissue Reservoirs, and Immunoregulatory Cells in Human Immunodeficiency Virus Disease," *Curr. Topics Microbiol. Immunol.* 181: 239–263 (1992).
Mukhergee & Heidelberger, *Cancer Res.* 22: 815–822 (1962).
Murray et al., "Experimental Visceral Leishmaniasis: Production of Interleukin 2 and Interferon y, Tissue Immune Reaction, and Response to Treatment with Interleukin 2 and Interferon y," *J Immunol.* 138: 2290–2296 (1987).
Narayan et al., "Lentivirus Induced Arthritis in Animals," *J Rheumatol.* 32: 25–32 (1992).
Negre et al., "Antileishmanial Drug Targeting through Glycosylated Polymers Specifically Internalized by Macrophage Membrane Lectins," *Antimicrob. Agents and Chemother.* 36: 2228–2232 (1992).
Neto et al., *Biochem. Biophys. Res. Commun.* 171: 458–464 (1990).
Ng & Heath, *Biochim. Biophys. Acta* 981: 261–268 (1989).
Nogueira and Cohn, "Trypanosoma cruzi: Mechanisms of Entry and Intracellular Fate in Mammalian Cells," *J Exp. Med.* 143: 1402–1420 (1976).
Nothnagel, *Biochim. Biophys. Acta* 980: 209–219 (1989).
Pagano et al., *J Biol. Chem.* 258: 2034–2040 (1983).
Panuska et al., "Productive Infection of Isolated Human Alveolar Macrophages by Respiratory Syncytial Virus," *J Clin. Invest.* 86: 113–119 (1990).
Pardridge, "Opioid Peptide Drug Development: Transport of Opioid Chimeric Peptides through the Blood–Brain Barrier," *NIDA Res. Monograph* 120: 153–168 (1992).
Paul and Anderson, *J Am. Chem. Soc.* 82: 4596–4600 (1960).
Payne et al., "Phagocytosis of Legionella pneumophila is Mediated by Human Monocyte Complement Receptors," *J Exp. Med.* 166: 1377–1389 (1987).
Rahman et al., *Life Sci.* 31: 2061–2071 (1982).
Remy et al., *J Org. Chem.* 27: 2491–2500 (1962).
Rosenberg et al., *J Neurochem.* 48: 865–875 (1987).
Rowlinson–Busza and Epenetos, "Targeted delivery of biologic and other antineoplastic agents," *Curr. Opin. Oncol.* 4: 1142–1148 (1992).
Rubinstein et al., "In Vitro Evaluation of Calcium Pectinate: A Potential Colon–Specific Drug Delivery Carrier," *Pharm. Res.* 10: 258–263 (1993).
Saffran et al., "A New Approach to the Oral Administration of Insulin and Other Peptide Drugs," *Science* 233: 1081–1084 (1986).
Salord et al., *Biochim. Biophys. Acta* 886: 64–75 (1986).
Schlessinger and Horwitz, "Phagocytosis of Leprosy Bacilli is Mediated by Complement Receptors CR1 and CR3 on Human Monocytes and Complement Component C3 in Serum," *J Clin. Invest.* 85: 1304–1314 (1990).
Schmitt et al., "Multiplication of Human Immunodeficiency Virus in Primary Cultures of Human Kupffer Cells –Possible Role of Liver Macrophage Infection in the Physiopathology of AIDS," *Res. Virol.* 141: 143–152 (1990).
Schnorr et al., "MxA–Dependent Inhibition of Measles Virus Glycoprotein Synthesis in a Stably Transfected Human Monocytic Cell Line," *J Virol.* 67: 4760–4768 (1993).
Sellon et al., "Wild–Type Equine Infectious Anemia Virus Replicates in Vivo Predominantly in Tissue Macrophages, Not in Peripheral Blood Monocytes," *J Virol.* 66: 5906–5913 (1992).
Senter et al., "Activation of Prodrugs by Antibody–Enzyme Conjugates," *in Immunobiology of Peptides and Proteins* vol. VI, pp. 97–105 (1991).
Shanley and Pesanti, "Murine Peritoneal Macrophages Support Murine Cytomegalovirus Replication," *Infect. Immunol.* 41: 1352–1359 (1983).
Shen et al., "Cis–Aconityl Spacer between Daunomycin and Macromolecular Carriers: A Model of pH Sensitive Linkage Releasing Drug from a Lysomotropic Conjugate," *Biochem. Biophys. Res. Commun.* 102: 1048–1052 (1981).
Sierra–Honigman et al., "Borna disease virus in peripheral blood mononuclear and bone marrow cells of neonatally and chronically infected rats," *J Neuroimmunol.* 45: 31–36 (1993).
Sintov et al., "Enzymatic cleavage of disaccharaide side groups in insoluble synthetic polymers: a new method for specific delivery of drugs to the colon," *Biomaterials* 14: 483–490 (1993).
Smith and Khorana, *J Amer. Chem. Soc.* 80: 1141–1145 (1958).
Steim et al., *Biochem. Biophys. Res. Commun.* 171: 451–457 (1990).
Strellrecht–Broomhall, "Evidence for Immune–Mediated Destruction as Mechanism for LCMV–Induced Anemia in Persistently Infected Mice," *Viral Immunol.* 4: 269–280 (1991).
Sturgill–Koszycki et al., "Lack of Acidification in Mycobacterium Phagosomes Produced by Exclusion of the Vesicular Proton–ATPase," *Science* 263: 678–681 (1994).

Trouet et al., "A covalent linkage between daunorubicin and proteins that is stable in serum and reversable by lysosomal hydrolases, as required for a lysomotropic drug–carrier conjugate: In vitro and in vivo studies," *Proc. Natl. Acad. Sci. USA* 79: 626–629 (1982).

van Wijk et al., *Biochim. Biophys. Acta* 1084: 307–310 (1991).

Verbloom et al., *Synthesis* 1032: 807–809 (1981).

Wada et al., "Salt Formation of Lactic Acid Oligomers as Matrix for Sustained Release of Drugs," *J Pharm. Pharmacol.* 43: 605–608 (1991).

Wyrick and Brownridge, "Growth of Chlamydia psittaci in Macrophages," *Infect. Immunol.* 19: 1054–1060 (1978).

Yatvin et al., "Targeting Lipophilic Prodrugs to Brain, Lung, and Spleen," *Journal of Cellular Biochemistry,* vol. 0, No. 19A: 173 (1995).

Yatvin, "A Multi–Modality Approach for the Treatment of AIDS," *Select. Cancer. Therapeut.* 7: 23–28 (1991).

Zasloff, "Magainins, a class of antimicrobial peptides from Xenopus skin: Isolation, characterization of two active forms, and partial cDNA sequence of a precursor," *Proc. Natl. Acad. Sci USA* 84: 5449–5453 (1987).

Zhang and McCormick, "Uptake of N–(4'–pyridoxyl)amines and release of amines by renal cells: A model for transporter–enhanced delivery of bioactive compounds," *Proc. Natl. Acad. Sci. USA* 88: 10407–10410 (1991).

COVALENT MICROPARTICLE-DRUG CONJUGATES FOR BIOLOGICAL TARGETING

This application is a continuation of U.S. patent application Ser. No. 08/441,770, filed May 16, 1995, now U.S. Pat. No. 5,543,391, issued Aug. 6, 1996, and U.S. patent application Ser. No. 08/246,941, filed May 19, 1994, now U.S. Pat. No. 5,543,390, issued Aug. 6, 1996, which is a continuation-in-part of U.S. patent application Ser. No. 08/142,771, filed Oct. 26, 1993, now U.S. Pat. No. 5,543,389, issued Aug. 6, 1996 which is a continuation-in-part of U.S. patent application Ser. No. 07/911,209, filed Jul. 9, 1992, now U.S. Pat. No. 5,256,641, issued Oct. 26, 1993, which was a continuation-in-part of U.S. patent application Ser. No. 07/607,982, filed Nov. 1, 1990, now U.S. Pat. No. 5,149,794, issued Sep. 22, 1992, each of which is herein incorporated by reference in its entirety.

This invention was made with government support under grant 1-RO1-CA49416 by the National Institutes of Health. The government has certain rights in the invention.

BACKGROUND OF THE INVENTION

1. Field of the Invention

This invention relates to methods of facilitating the entry of biologically-active compounds into phagocytic cells and for targeting such compounds to specific organelles within the cell. The invention specifically provides compositions of matter and pharmaceutical embodiments of such compositions comprising conjugates of such biologically-active compounds covalently linked to particulate carriers generally termed microparticles. Particular embodiments of such compositions include compositions wherein the biologically-active compounds are antiviral and antimicrobial drugs or agents. In such compositions the microparticle is coated with an antiviral or antimicrobial drug, and then further coated with organic coating material that is the target of a microorganism-specific protein having enzymatic activity. Thus, the invention provides cell targeting of drugs wherein the targeted drug is only released in cells infected with a particular microorganism. Alternative embodiments of such specific drug delivery compositions also contain polar lipid carrier molecules. Particular embodiments of such conjugates comprise a coated microparticle wherein an antiviral or antimicrobial drug is covalently linked to a polar lipid compound and the particle further coated with an organic coating material, to facilitate targeting of such drugs or agents to particular subcellular organelles within the cell.

2. Background of the Related Art

A major goal in the pharmacological arts has been the development of methods and compositions to facilitate the specific delivery of therapeutic and other agents to the appropriate cells and tissues that would benefit from such treatment, and the avoidance of the general physiological effects of the inappropriate delivery of such agents to other cells or tissues of the body. The most common example of the need for such specificity is in the field of antibiotic therapy, in which the amount of a variety of antibiotic, antiviral and antimicrobial agents that can be safely administered to a patient is limited by their cytotoxic and immunogenic effects.

It is also recognized in the medical arts that certain cells and subcellular organelles are the sites of pharmacological action of certain drugs or agents or are involved in the biological response to certain stimuli. In particular, it is now recognized that certain cell types and subcellular organelles within such cell types are reservoirs for occult infection that evades normal immune surveillance and permits the persistence of chronic infections. Specific delivery of diagnostic or therapeutic compounds to such intracellular organelles is thus desirable to increase the specificity and effectiveness of such clinical diagnostic or therapeutic techniques.

A. Drug Targeting

It is desirable to increase the efficiency and specificity of administration of a therapeutic agent to the cells of the relevant tissues in a variety of pathological states. This is particularly important as relates to antiviral and antimicrobial drugs or agents. These drugs or agents typically have pleiotropic antibiotic and cytotoxic effects that damage or destroy uninfected cells as well as infected cells. Thus, an efficient delivery system which would enable the delivery of such drugs or agents specifically to infected cells would increase the efficacy of treatment and reduce the associated "side effects" of such drug treatments, and also serve to reduce morbidity and mortality associated with clinical administration of such drugs or agents.

Numerous methods for enhancing the cytotoxic activity and the specificity of antibiotic drug action have been proposed. One method, receptor targeting, involves linking the therapeutic agent to a ligand which has an affinity for a receptor expressed on the desired target cell surface. Using this approach, an antimicrobial agent or drug is intended to adhere to the target cell following formation of a ligand-receptor complex on the cell surface. Entry into the cell could then follow as the result of internalization of ligand-receptor complexes. Following internalization, the antimicrobial drug may then exert its therapeutic effects directly on the cell.

One limitation of the receptor targeting approach lies in the fact that there are only a finite number of receptors on the surface of target cells. It has been estimated that the maximum number of receptors on a cell is approximately one million (Darnell et al., 1986, *Molecular Cell Biology*, 2d ed., W. H. Freeman: New York, 1990). This estimate predicts that there may be a maximum one million drug-conjugated ligand-receptor complexes on any given cell. Since not all of the ligand-receptor complexes may be internalized, and any given ligand-receptor system may express many-fold fewer receptors on a given cell surface, the efficacy of intracellular drug delivery using this approach is uncertain. Other known intracellular ligand-receptor complexes (such as the steroid hormone receptor) express as few as ten thousand hormone molecules per cell. Id. Thus, the ligand-receptor approach is plagued by a number of biological limitations.

Other methods of delivering therapeutic agents at concentrations higher than those achievable through the receptor targeting process include the use of lipid conjugates that have selective affinities for specific biological membranes. These methods have met with little success. (see, for example, Remy et al., 1962, *J. Org. Chem.* 27:2491–2500; Mukhergee & Heidelberger, 1962, *Cancer Res.* 22:815–22; Brewster et al., 1985, *J. Pharm. Sci.* 17:981–985).

Liposomes have also been used to attempt cell targeting. Rahman et al., 1982, *Life Sci. 31:2061–71* found that liposomes which contained galactolipid as part of the lipid appeared to have a higher affinity for parenchymal cells than liposomes which lacked galactolipid. To date, however, efficient or specific drug delivery has not been predictably achieved using drug-encapsulated liposomes. There remains a need for the development of cell-specific and organelle-specific targeting drug delivery systems.

B. Phagocytic Cell-Specific Targeting

Cell-specific targeting is also an important goal of antimicrobial therapy, particularly in the event that a specific cell type is a target of acute or chronic infection. Targeting in the case of infection of a specific cell type would be advantageous because it would allow administration of biologically-toxic compounds to an animal suffering from infection with a microbial pathogen, without the risk of non-specific toxicity to uninfected cells that would exist with nontargeted administration of the toxic compound. An additional advantage of such targeted antimicrobial therapy would be improved pharmacokinetics that would result from specific concentration of the antimicrobial agent to the sites of infection, i.e., the infected cells.

Phagocytic cells such as monocytes and macrophages are known to be specific targets for infection of certain pathogenic microorganisms.

Sturgill-Koszycki et al., 1994, Science 263:678–681 disclose that the basis for lack of acidification of phagosomes in M. avium and M. tuberculosis-infected macrophages is exclusion of the vesicular proton-ATPase.

Sierra-Honigman et al., 1993, J. Neuroimmunol. 45:31–36 disclose Borna disease virus infection of monocytic cells in bone marrow.

Maciejewski et al., 1993, Virol. 195:327–336 disclose human cytomegalovirus infection of mononucleated phagocytes in vitro.

Alvarez-Dominguez et al., 1993, Infect. Immun. 61:3664–3672 disclose the involvement of complement factor Clq in phagocytosis of Listeria monocytogenes by macrophages.

Kanno et al., 1993, J. Virol. 67:2075–2082 disclose that Aleutian mink disease parvovirus replication depends on differentiation state of the infected macrophage.

Kanno et al., 1992, J. Virol. 66:5305–5312 disclose that Aleutian mink disease parvovirus infects peritoneal macrophages in mink.

Narayan et al., 1992, J. Rheumatol. 32:25–32 disclose arthritis in animals caused by infection of macrophage precursors with lentivirus, and activation of quiescent lentivirus infection upon differentiation of such precursor cells into terminally-differentiated macrophages.

Horwitz, 1992, Curr. Top. Microbiol. Immunol. 181:265–282 disclose Legionella pneumophila infections of alveolar macrophages as the basis for Legionnaire's disease and Pontiac fever.

Sellon et al., 1992, J. Virol. 66:5906–5913 disclose equine infectious anemia virus replicates in tissue macrophages in vivo.

Groisman et al., 1992, Proc. Natl. Acad. Sci. USA 89:11939–11943 disclose that S. typhimurium survives inside infected macrophages by resistance to antibacterial peptides.

Friedman et al., 1992, Infect. Immun. 60:4578–4585 disclose Bordetella pertussis infection of human macrophages.

Stellrecht-Broomhall, 1991, Viral Immunol. 4:269–280 disclose that lymphocytic choriomeningitis virus infection of macrophages promotes severe anemia caused by macrophage phagocytosis of red blood cells.

Frehel et al., 1991, Infect. Immun. 59: 2207–2214 disclose infection of spleen and liver-specific inflammatory macrophages by Mycobacterium avium, the existence of the microbe in encapsulated phagosomes within the inflammatory macrophages and survival therein in phagolysosomes.

Bromberg et al., 1991, Infect. Immun. 59:4715–4719 disclose intracellular infection of alveolar macrophages.

Mauel, 1990, J. Leukocyte Biol. 47:187–193 disclose that Leishmania spp. are intracellular parasites in macrophages.

Buchmeier and Heffron, 1990, Science 248:730–732 disclose that Salmonella typhimurium infection of macrophages induced bacterial stress proteins.

Panuska et al., 1990, J. Clin. Invest. 86:113–119 disclose productive infection of alveolar macrophages by respiratory syncytial virus.

Cordier et al., 1990, Clin. Immunol. Immunopathol. 55:355–367 disclose infection of alveolar macrophages by visna-maedi virus in chronic interstitial lung disease in sheep.

Schlessinger and Horwitz, 1990, J. Clin. Invest. 85:1304–1314 disclose Mycobacterium leprae infection of macrophages.

Clarke et al., 1990, AIDS 4:1133–1136 disclose human immunodeficiency virus infection of alveolar macrophages in lung.

Baroni et al., 1988, Am. J. Pathol. 133:498–506 disclose human immunodeficiency virus infection of lymph nodes.

Payne et al, 1987, J. Exp. Med. 166:1377–1389 disclose Mycobactertium tuberculosis infection of macrophages.

Murray et al., 1987, J. Immunol. 138:2290–2296 disclose that liver Kupffer cells are the initial targets for L. donovani infection.

Koenig et al., 1986, Science 233:1089–1093 disclose human immunodeficiency virus infection of macrophages in the central nervous system.

Horwitz and Maxfield, 1984, J. Cell Biol. 99:1936–1943 disclose that L. pneumophila survives in infected phagocytic cells at least in part by inhibiting reduction of intraphagosomic hydrogen ion concentration (pH).

Shanley and Pesanti, 1983, Infect. Immunol. 41:1352–1359 disclose cytomegalovirus infection of macrophages in murine cells.

Horwitz, 1983, J. Exp. Med. 158:2108–2126 disclose that L. pneumophila is an obligate intracellular parasite that is phagocytized into a phagosome wherein fusion with lysosome is inhibited.

Chang, 1979, Exp. Parisitol. 48:175–189 disclose Leischmania donovani infection of macrophages.

Wyrick and Brownridge, 1978, Infect. Immunol. 19:1054–1060 disclose Chlamydia psittaci infection of macrophages.

Nogueira and Cohn, 1976, J. Exp. Med. 143:1402–1420 disclose Trypanosoma cruzi infection of macrophages.

Jones and Hirsch, 1972, J. Exp. Med. 136:1173–1194 disclose Toxoplasma gondii infection of macrophages.

Persistent infection of phagocytic cells has been reported in the prior art.

Embretson et al., 1993, Nature 362:359–361 disclose covert infection of macrophages with HIV and dissemination of infected cells throughout the immune system early in the course of disease.

Schnorr et al., 1993, J. Virol. 67:4760–4768 disclose measles virus persistent infection in vitro in a human monocytic cell line.

Meltzer and Gendelman, 1992, Curr. Topics Microbiol. Immunol. 181:239–263 provide a review of HIV infection of tissue macrophages in brain, liver, lung, skin, lymph nodes, and bone marrow, and involvement of macrophage infection in AIDS pathology.

Blight et al., 1992, Liver 12:286–289 disclose persistent infection of liver macrophages (Kuppfer cells) by hepatitis C virus.

McEntee et al., 1991, *J. gen. Virol.* 72:317–324 disclose persistent infection of macrophages by HIV resulting in destruction of T lymphocytes by fusion with infected macrophages, and that the macrophages survive fusion to kill other T lymphocytes.

Kondo et al., 1991, *J. gen. Virol.* 72:1401–1408 disclose herpes simplex virus 6 latent infection of monocytes activated by differentiation into macrophages.

King et al., 1990, *J. Virol.* 64:5611–5616 disclose persistent infection of macrophages with lymphocytic choriomeningitis virus.

Schmitt et al., 1990, *Res. Virol.* 141:143–152 disclose a role for HIV infection of Kupffer cells as reservoirs for HIV infection.

Gendelman et al., 1985, *Proc. Natl. Acad. Sci. USA* 82:7086–7090 disclose lentiviral (visna-maedi) infection of bone marrow precursors of peripheral blood monocytes/macrophages that provide a reservoir of latently-infected cells.

Halstead et al., 1977, *J. Exp. Med.* 146:201–217 disclose that macrophages are targets of persistent infection with dengue virus.

Mauel et al., 1973, *Nature New Biol.* 244:93–94 disclose that lysis of infected macrophages with sodium dodecyl sulfate could release live microbes.

Attempts at drug targeting have been reported in the prior art.

Rubinstein et al., 1993, *Pharm. Res.* 10:258–263 report colon targeting using calcium pectinate (CaPec)-conjugated drugs, based on degradation of CaPec by colon specific (i.e., microflora-specific) enzymes and a hydrophobic drug incorporated into the insoluble CaPec matrices.

Sintov et al., 1993, *Biomaterials* 14:483–490 report colon-specific targeting using conjugation of drug to insoluble synthetic polymer using disaccharide cleaved by enzymes made by intestinal microflora, specifically, P-glycosidic linkages comprising dextran.

Franssen et al., 1992, *J. Med. Chem.* 35:1246–1259 report renal cell/kidney drug targeting using low molecular weight proteins (LMWP) as carriers, using enzymatic/chemical hydrolysis of a spacer molecule linking the drug and LMWP carrier.

Bai et al., 1992, *J. Pharm. Sci.* 81:113–116 report intestinal cell targeting using a peptide carrier-drug system wherein the conjugate is cleaved by an intestine-specific enzyme, prolidase.

Gaspar et al., 1992, *Ann. Trop. Med. Parasitol.* 86:41–49 disclose primaquine-loaded polyisohexylcyanoacrylate nanoparticles used to target *Leschmania donovani* infected macrophage-like cells in vitro.

Pardridge, 1992, *NIDA Res. Monograph* 120:153–168 report opioid-conjugated chimeric peptide carriers for targeting to brain across the blood-brain barrier.

Bai and Amidon, 1992, *Pharm. Res.* 9:969–978 report peptide-drug conjugates for oral delivery and intestinal mucosal targeting of drugs.

Ashbom et al., 1991, *J. Infect. Dis.* 163:703–709 disclose the use of CD4-conjugated *Pseudomonas aeruginosa* exotoxin A to kill HIV-infected macrophages.

Larsen et al., 1991, *Acta Pharm. Nord.* 3:41–44 report enzyme-mediated release of drug from dextrin-drug conjugates by microflora-specific enzymes for colon targeting.

Faulk et al., 1991, *Biochem. Int.* 25:815–822 report adriamycin-transferrin conjugates for tumor cell growth inhibition in vitro.

Zhang and McCormick, 1991, *Proc. Natl. Acad. Sci. USA* 88:10407–10410 report renal cell targeting using vitamin B6-drug conjugates.

Blum et al., 1982, *Int. J. Pharm.* 12:135–146 report polystyrene microspheres for specific delivery of compounds to liver and lung.

Trouet et al., 1982, *Proc. Natl. Acad. Sci. USA* 79:626–629 report that daunorubicin-conjugated to proteins were cleaved by lysosomal hydrolases in vivo and in vitro.

Shen et al., 1981, *Biochem. Biophys. Res. Commun.* 102:1048–1052 report pH-labile N-cis-acontinyl spacer moieties.

Monoclonal antibodies have been used in the prior art for drug targeting.

Serino et al, U.S. Pat. No. 4,793,986, issued Dec. 27, 1988, provides platinum anticancer drugs conjugated to polysaccharide (dextrin) carrier for conjugation to monoclonal antibodies for tumor cell targeting.

Bickel et al., 1993, *Proc. Natl. Acad. Sci. USA* 90:2618–2622 discloses the use of a chimeric protein vector for targeting across blood-brain barrier using anti-transferrin monoclonal antibody.

Rowlinson-Busza and Epenetos, 1992, *Curr. Opin. Oncol.* 4:1142–1148 provides antitumor immunotargeting using toxin-antibody conjugates.

Blakey, 1992, *Acta Oncol.* 31:91–97 provides a review of antitumor antibody targeting of antineoplastic drugs.

Senter et al., 1991, in *Immunobiology of Peptides and Proteins*, Vol. VI, pp.97–105 discloses monoclonal antibodies linked to alkaline phosphatase or penicillin-V amidase to activate prodrugs specifically at site of antibody targeting, for therapeutic treatment of solid tumors.

Drug-carrier conjugates have been used in the prior art to provide time-release drug delivery agents.

Couveur and Puisieux, 1993, *Adv. Drug Deliv. Rev.* 10:141–162 provide a review of microcapsule (vesicular), microsphere (dispersed matrix) and microparticle (1–250 μm)-based drug delivery systems, based on degradation of particle with drug release, to provide time release of drugs, oral delivery via transit through the intestinal mucosa and delivery to Kupffer cells of liver.

Duncan, 1992, *Anticancer Drugs* 3:175–210 provide a review of improved pharmicokinetic profile of in vivo drug release of anticancer drugs using drug-polymer conjugates.

Heinrich et al., 1991, *J. Pharm. Pharmacol.* 43:762–765 disclose poly-lactide-glycolide polymers for slow release of gonadotropin releasing hormone agonists as injectable implants.

Wada et al. 1991, *J. Pharm. Pharmacol.* 43:605–608 disclose sustained-release drug conjugates with lactic acid oligomers.

Specifically, polymer-conjugated drugs have been reported in the prior art, and attempts to adapt particulate conjugates have also been reported.

Ryser et al., U.S. Pat. No. 4,847,240, issued Jul. 11, 1989, provides cationic polymers for conjugation to compounds that are poorly transported into cells. Examples include the antineoplastic drug methotrexate conjugated with polylysine and other polycationic amino acids are the carriers.

Ellestad et al., U.S. Pat. No. 5,053,394, issued Oct. 1, 1991, provides carrier-drug conjugates of methyltrithiol antibacterial and antitumor agents with a spacer linked to a targeting molecule which is an antibody or fragment thereof, growth factors or steroids.

Kopecek et al., U.S. Pat. No. 5,258,453, issued Nov. 2, 1993, provides antitumor compositions comprising both an anticancer drug and a photoactivatable drug attached to a copolymeric carrier by functional groups labile in cellular lysosomes, optionally containing a targeting moiety that are monoclonal antibodies, hormones, etc.

Negre et al., 1992, *Antimicrob. Agents and Chemother.* 36:2228–2232 disclose the use of neutral mannose-substituted polylysine conjugates with an anti-leischmanial drug (allopurinol riboside) to treat murine infected macrophages in vitro.

Yatvin, 1991, *Select. Cancer. Therapeut.* 7:23–28 discusses the use of particulate carriers for drug targeting.

Hunter et al., 1988, *J. Pharm. Phamacol.* 40:161–165 disclose liposome-mediated delivery of anti-leischmanial drugs to infected murine macrophages in vitro.

Saffran et al., 1986, *Science* 2:1081–1084 disclose drug release from a particulate carrier in the gut resulting from degradation of the carrier by enzymes produced by intestinal microflora.

SUMMARY OF THE INVENTION

The present invention is directed to an improved method for delivering biologically-active compounds to phagocytic cells and cellular organelles of such phagocytic cells in vivo and in vitro. This delivery system achieves such specific delivery of biologically-active compounds to phagocytic cells through conjugating the compound with a particular microparticle via an cleavable linker moiety. Alternatively, specific delivery is achieved by impregnating the biological compound into a porous microparticle which is then coated with an organic coating material. In an alternative embodiment, the delivery system comprises a nonporous microparticle wherein a biologically-active compound is made to coat the particle, and the particle is then further coated by an organic coating material. In each case, specific release of biologically-active compounds is achieved by enzymatic or chemical release of the biological compound from the microparticle by cleavage of the cleavable linker moiety or the organic coating material in specific phagocytic cells.

Additionally, such cell-targeted biologically-active compounds are further targeted to specific subcellular organelles through conjugating the compounds with a polar lipid carrier. This invention has the specific advantage of facilitating the delivery of such compounds to specific subcellular organelles via the polar lipid carrier, achieving effective intracellular concentrations of such compounds more efficiently and with more specificity than conventional delivery systems.

The specific delivery of biologically-active compounds achieved by the present invention results from the conjugation of biologically-active compounds to microparticles. Specific intracellular accumulation and facilitated cell entry is mediated by the phagocytic uptake of microparticle-conjugated biologically active compounds by such cells. Preferred embodiments of phagocytic cellular targets include phagocytic hematopoietic cells, preferably macrophages and phagocytic neutrophiles.

Particularly preferred targets of the microparticle-conjugated biologically active compounds of the invention are phagocytic cells, preferably macrophages and phagocytic neutrophiles that are infected with any of a variety of pathological or disease-causing microorganisms. For such cells, the embodiments of the microparticle-conjugated biologically active compounds of the invention are comprised of cleavable linker moieties whereby chemical or enzymatic cleavage of said linker moieties is specific for infected phagocytic cells. This provides for the specific release of biologically-active compounds, such as antiviral and antimicrobial drugs or agents, to such infected cells. It is understood that all phagocytic cells will take up such antiviral and antimicrobial embodiments of the microparticle-conjugated biologically active compounds of the invention. However, it is an advantageous feature of the microparticle-conjugated biologically active compounds of the invention that specific release of biologically-active forms of such antiviral and antimicrobial drugs or agents is dependent on the presence of the infectious microorganism in the phagocytic cell.

The invention also provides compositions of matter comprising a porous microparticle into which is impregnated a biologically-active compound, the impregnated porous microparticle being further coated with an organic coating material. In this aspect of the invention, the organic coating material is specifically degraded inside a phagocytic mammalian cell infected with a microorganism, allowing the release of the biologically-active compound within the infected cell. In preferred embodiments, the organic coating material is a substrate for a protein having an enzymatic activity found specifically in phagocytic cells infected with a pathological or disease-causing microorganism. In additional preferred embodiments, the organic coating material is chemically cleaved under physiological conditions that are specific for phagocytic cells infected with a pathological or disease-causing microorganism.

Preferred biologically active compounds used to impregnate such porous microparticles include antiviral and antimicrobial compounds, drugs, peptides, toxins and other antibiotic agents.

The biologically active compounds of the invention impregnated within porous microparticles may optionally be covalently linked to a polar lipid moiety. Polar lipid moieties comprise one or a plurality of polar lipid molecules. Polar lipid moieties are comprised of one or a plurality of polar lipid molecules of the invention covalently linked to a biologically-active compound, optionally via an organic a spacer molecule having two linker functional groups, wherein the spacer has a first end and a second end and wherein the polar lipid moiety is attached to the first end of the spacer through a first linker functional group and the biologically-active compound is attached to the second end of the spacer through a second linker functional group. In a particular embodiment of this aspect of the invention, the spacer allows the biologically-active compound to act at an intracellular site after being released from the microparticle but without being released from the intracellular targeting polar lipid moiety. In these embodiments of the invention, the first linker functional group attached to the first end of the spacer is characterized as "strong" and the second linker functional group attached to the second end of the spacer is characterized as "weak", with reference to the propensity of the covalent bonds between each end of the spacer molecule to be broken.

In other embodiments of the compositions of matter of the invention, the organic spacer allows the facilitated hydrolytic release of the biologically-active compound at an intracellular site after infection-specific intracellular release of the drug from the microparticle. Other embodiments of the spacer facilitate the enzymatic release of the biologically-active compound at an intracellular site after infection-specific intracellular release of the drug from the microparticle.

In a particular embodiment of this aspect of the invention, the organic spacer molecule is a peptide of formula (amino acid)$_n$, wherein n is an integer between 2 and 100, preferably wherein the peptide comprises a polymer of one or more amino acids.

In other embodiments of the compositions of matter of the invention, the biologically-active compound of the invention has a first functional linker group, and a polar lipid moiety has a second functional linker group, and the compound is directly covalently linked to the polar lipid moiety by a chemical bond between the first and second functional linker groups. In such embodiments, either the biologically-active compound or the polar lipid moiety comprises yet another functional linker group which is directly covalently linked to the cleavable linker moiety of the invention, which in turn is covalently linked to the microparticle. In preferred embodiments, each of the functional linker groups is a hydroxyl group, a primary or secondary amino group, a phosphate group or substituted derivatives thereof or a carboxylic acid group.

Preferred polar lipids include but are not limited to acyl carnitine, acylated carnitine, sphingosine, ceramide, phosphatidyl choline, phosphatidyl glycerol, phosphatidyl ethanolamine, phosphatidyl inositol, phosphatidyl serine, cardiolipin and phosphatidic acid.

The invention also provides compositions of matter comprising a nonporous microparticle onto which is coated a biologically-active compound, the coated nonporous microparticle being further coated with an organic coating material. In this aspect of the invention, the organic coating material is specifically degraded inside a phagocytic mammalian cell infected with a microorganism, allowing the release of the biologically-active compound within the infected cell. In preferred embodiments, the organic coating material is a substrate for a protein having an enzymatic activity found specifically in phagocytic cells infected with a pathological or disease-causing microorganism. In additional preferred embodiments, the organic coating material is chemically cleaved under physiological conditions that are specific for phagocytic cells infected with a pathological or disease-causing microorganism.

Preferred biologically active compounds used to coat such nonporous microparticles include antiviral and antimicrobial compounds, drugs, peptides, toxins and other antibiotic agents.

The biologically active compounds of the invention coated onto nonporous microparticles may optionally be covalently linked to a polar lipid moiety. Polar lipid moieties comprise one or a plurality of polar lipid molecules. Polar lipid moieties are comprised of one or a plurality of polar lipid molecules of the invention covalently linked to a biologically-active compound, optionally via an organic a spacer molecule having two linker functional groups, wherein the spacer has a first end and a second end and wherein the polar lipid moiety is attached to the first end of the spacer through a first linker functional group and the biologically-active compound is attached to the second end of the spacer through a second linker functional group. In a particular embodiment of this aspect of the invention, the spacer allows the biologically-active compound to act at an intracellular site after being released from the microparticle but without being released from the intracellular targeting polar lipid moiety. In these embodiments of the invention, the first linker functional group attached to the first end of the spacer is characterized as "strong" and the second linker functional group attached to the second end of the spacer is characterized as "weak", with reference to the propensity of the covalent bonds between each end of the spacer molecule to be broken.

In other embodiments of the compositions of matter of the invention, the organic spacer allows the facilitated hydrolytic release of the biologically-active compound at an intracellular site after infection-specific intracellular release of the drug from the microparticle. Other embodiments of the spacer facilitate the enzymatic release of the biologically-active compound at an intracellular site after infection-specific intracellular release of the drug from the microparticle.

In a particular embodiment of this aspect of the invention, the organic spacer molecule is a peptide of formula (amino acid)$_n$, wherein n is an integer between 2 and 100, preferably wherein the peptide comprises a polymer of one or more amino acids.

In other embodiments of the compositions of matter of the invention, the biologically-active compound of the invention has a first functional linker group, and a polar lipid moiety has a second functional linker group, and the compound is directly covalently linked to the polar lipid moiety by a chemical bond between the first and second functional linker groups. In such embodiments, either the biologically-active compound or the polar lipid moiety comprises yet another functional linker group which is directly covalently linked to the cleavable linker moiety of the invention, which in turn is covalently linked to the microparticle. In preferred embodiments, each of the functional linker groups is a hydroxyl group, a primary or secondary amino group, a phosphate group or substituted derivatives thereof or a carboxylic acid group.

Preferred polar lipids include but are not limited to acyl carnitine, acylated carnitine, sphingosine, ceramide, phosphatidyl choline, phosphatidyl glycerol, phosphatidyl ethanolamine, phosphatidyl inositol, phosphatidyl serine, cardiolipin and phosphatidic acid.

In this aspect of the invention, the biologically-active compound will be understood to dissolve from the surface of the microparticle upon enzymatic or chemical degradation of the organic coating material. Release of the biologically-active compound can be accomplished simply be mass action, i.e., whereby the compound dissolves from the surface of the nonporous microparticle into the surrounding cytoplasm within the cell.

The invention also provides compositions of matter comprising a biologically-active compound linked to a microparticle via a cleavable linker moiety. The cleavable linker moieties of the invention comprise two linker functional groups, wherein the cleavable linker moiety has a first end and a second end. The microparticle is attached to the first end of the cleavable linker moiety through a first linker functional group and the biologically-active compound is attached to the second end of the cleavable linker moiety through a second linker functional group. The cleavable linker moieties of the invention are specifically cleaved inside a phagocytic mammalian cell, for example, a phagocytic cell infected with a microorganism. In preferred embodiments, the cleavable linker moieties of the invention comprise a substrate for a protein having an enzymatic activity found specifically in phagocytic cells infected with a pathological or disease-causing microorganism. In additional preferred embodiments, the cleavable linker moieties of the invention comprise a moiety that is chemically cleaved under physiological conditions that are specific for phagocytic cells infected with a pathological or disease-causing microorganism.

The invention also provides microparticle-conjugated biologically active compounds covalently linked to a polar lipid moiety. Polar lipid moieties comprise one or a plurality of polar lipid molecules. Polar lipid moieties are comprised of one or a plurality of polar lipid molecules of the invention covalently linked to a biologically-active compound, an cleavable linker moiety, or each other.

In preferred embodiments of the invention, the biologically-active compound is a peptide. In other preferred embodiments, the biologically-active compound is a drug, most preferably an antiviral or antimicrobial drug. Preferred polar lipids include but are not limited to acyl carnitine, acylated carnitine, sphingosine, ceramide, phosphatidyl choline, phosphatidyl glycerol, phosphatidyl ethanolamine, phosphatidyl inositol, phosphatidyl serine, cardiolipin and phosphatidic acid.

Additional embodiments of the microparticle-conjugated biologically active compounds of the invention also comprise a spacer molecule having two linker functional groups, wherein the spacer has a first end and a second end and wherein the polar lipid moiety is attached to the first end of the spacer through a first linker functional group and the biologically-active compound is attached to the second end of the spacer through a second linker functional group. In a particular embodiment of this aspect of the invention, the spacer allows the biologically-active compound to act at an intracellular site after being released from the microparticle but without being released from the intracellular targeting polar lipid moiety. In these embodiments of the invention, the first linker functional group attached to the first end of the spacer is characterized as "strong" and the second linker functional group attached to the second end of the spacer is characterized as "weak", with reference to the propensity of the covalent bonds between each end of the spacer molecule to be broken.

In other embodiments of the compositions of matter of the invention, the spacer allows the facilitated hydrolytic release of the biologically-active compound at an intracellular site after infection-specific intracellular release of the drug from the microparticle. Other embodiments of the spacer facilitate the enzymatic release of the biologically-active compound at an intracellular site after infection-specific intracellular release of the drug from the microparticle.

In a particular embodiment of this aspect of the invention, the spacer molecule is a peptide of formula (amino acid)$_n$, wherein n is an integer between 2 and 100, preferably wherein the peptide comprises a polymer of one or more amino acids.

In other embodiments of the compositions of matter of the invention, the biologically-active compound of the invention has a first functional linker group, and a polar lipid moiety has a second functional linker group, and the compound is directly covalently linked to the polar lipid moiety by a chemical bond between the first and second functional linker groups. In such embodiments, either the biologically-active compound or the polar lipid moiety comprises yet another functional linker group which is directly covalently linked to the cleavable linker moiety of the invention, which in turn is covalently linked to the microparticle. In preferred embodiments, each of the functional linker groups is a hydroxyl group, a primary or secondary amino group, a phosphate group or substituted derivatives thereof or a carboxylic acid group.

In another aspect of the invention is provided compositions of matter comprising a drug covalently linked to a cleavable linker moiety which in turn is linked to a microparticle. In preferred embodiments, the drug is an antiviral or antimicrobial drug. In particular embodiments of this aspect of the invention, the drug is covalently linked to a polar lipid moiety. Preferred embodiments also comprise an organic spacer moiety having a first and second functional linker group and wherein the drug has a functional linker group, wherein the drug is covalently linked to the organic spacer moiety by a chemical bond between the first functional linker group of the organic spacer moiety and the functional linker group of the drug. In such embodiments, the polar lipid moiety is also comprised of a functional linker group, and the second functional linker group of the organic spacer moiety is covalently linked to the polar lipid moiety by a chemical bond between the second functional linker group of the cleavable linker moiety and the functional linker group of the polar lipid moiety. In such embodiments, either the drug or the polar lipid moiety comprises yet another functional linker group which is directly covalently linked to the cleavable linker moiety of the invention, which in turn is covalently linked to the microparticle. In preferred embodiments, each of the functional linker groups is a hydroxyl group, a primary or secondary amino group, a phosphate group or substituted derivatives thereof or a carboxylic acid group. Preferred polar lipids include but are not limited to acyl carnitine, acylated carnitine, sphingosine, ceramide, phosphatidyl choline, phosphatidyl glycerol, phosphatidyl ethanolamine, phosphatidyl inositol, phosphatidyl serine, cardiolipin and phosphatidic acid.

In this aspect of the invention is provided compositions of matter comprising a drug, preferably an antiviral or antimicrobial drug, covalently linked to a microparticle via a cleavable linker moiety that is specifically cleaved in a phagocytic cell infected with a pathological or disease-causing microorganism. In additional embodiments of this aspect of the invention, the antiviral or antimicrobial drug is covalently linked to a polar lipid moiety via an organic spacer moiety wherein the spacer allows the drug to act without being released at an intracellular site, after being released from the microparticle but without being released from the intracellular targeting polar lipid moiety. In these embodiments of the invention, the first linker functional group attached to the first end of the spacer is characterized as "strong" and the second linker functional group attached to the second end of the spacer is characterized as "weak", with reference to the propensity of the covalent bonds between each end of the spacer molecule to be broken.

In other embodiments of the compositions of matter of the invention, the spacer allows the facilitated hydrolytic release of the antiviral or antimicrobial drug at an intracellular site after being released from the microparticle but without being released from the intracellular targeting polar lipid moiety. Other embodiments of the spacer facilitate the enzymatic release of the antiviral or antimicrobial drugs or agents of the invention at an intracellular site.

In still further embodiments of the compositions of matter of the invention, each of the antiviral and antimicrobial drugs or agents of the invention a first functional linker group, and a polar lipid moiety has a second functional linker group, and the antiviral or antimicrobial drug is directly covalently linked to the polar lipid moiety by a chemical bond between the first and second functional linker groups. In such embodiments, either the antiviral or antimicrobial drug or the polar lipid moiety comprises yet another functional linker group which is directly covalently linked to the cleavable linker moiety of the invention, which in turn is covalently linked to the microparticle. In preferred embodiments, each of the functional linker groups is a hydroxyl group, a primary or secondary amino group, a phosphate group or substituted derivatives thereof or a carboxylic acid group.

In another embodiment of this aspect of the invention, the organic spacer moiety is a peptide of formula (amino acid)$_n$, wherein n is an integer between 2 and 100, preferably wherein the peptide comprises a polymer of one or more amino acids.

As disclosed herein, the invention comprehends a conjugate between a microparticle and a biologically-active compound, preferably a drug, more preferably an antiviral or antimicrobial drug that is specifically taken up by phagocytic mammalian cells. In the microparticle-biologically-active compound conjugates of the invention are comprised of a cleavable linker moiety that is specifically cleaved in particular phagocytic cells, preferably microbially-infected cells. In additional embodiments, the biologically-active compounds of the invention are covalently linked to a polar lipid moiety wherein the lipid will selectively associate with certain biological membranes, and thereby facilitate subcellular targeting of the drug into specific subcellular organelles. The spacer component of the conjugates of the invention will preferably act to release the drug from the lipid, target the conjugate to a subcellular organelle, incorporate the drug into a viral envelope, or perform other functions to maximize the effectiveness of the drug, all after being released from the microparticle but without being released from the intracellular targeting polar lipid moiety.

The microparticle-drug conjugates of this invention have numerous advantages. First, the drug-microparticle conjugates are specifically taken up by phagocytic mammalian cells. Also, drugs, preferably antiviral and antimicrobial drugs or agents comprising the drug-microparticle conjugates of the invention, are linked to the microparticle by an organic linker that is specifically cleaved upon entry into appropriate phagocytic cells, for example, phagocytic cells infected with a pathological or disease-causing microorganism. Third, the drug-polar lipid conjugates of the invention will promote the intracellular targeting of a variety of potentially useful antiviral or antimicrobial drugs or agents at pharmokinetic rates not currently attainable. In this aspect, the range of targeted subcellular organelles is not limited per se by, for example, any particular, limited biological properties of the subcellular organelle such as the number and type of specific receptor molecules expressed by the organelle. In contrast to traditional attempts to simply target drugs or agents to specific cells, this method may target drugs or agents to specific intracellular organelles and other intracellular compartments. Fourth, the compositions of matter of the invention incorporate a variable spacer region that may allow pharmacologically-relevant rates of drug release from polar lipid moieties to be engineered into the compositions of the invention, thereby increasing their clinical efficacy and usefulness. Thus, time-dependent drug release and specific drug release in cells expressing the appropriate degradative enzymes are a unique possibility using the microparticle-drug-lipid conjugates of the invention. Fifth, the conjugates of the invention can be combined with other drug delivery approaches to further increase specificity and to take advantage of useful advances in the art. One example of antiviral therapy would involve incorporating the conjugates of the invention into the viral envelope, thereby directly modifying its lipid composition and influencing viral infectivity. Finally, the prodrug-microparticle conjugates of the invention are intended to encompass prodrugs which are biologically inactive unless and until pathogen-infection specific chemical or enzymatic cleavage into an active drug form inside a phagocytic mammalian cell.

Thus, the invention also provides a method of killing a microorganism infecting a mammalian cell. This method comprises contacting an infected phagocytic mammalian cells with the compositions of matter of the invention. The invention also provides a method for treating a microbial infection in a human wherein the infecting microbe is present inside a phagocytic cell in the human, the method comprising administering a therapeutically effective amount of the compositions of matter of the invention to the human in a pharmaceutically acceptable carrier. Thus, the invention also provides pharmaceutical compositions comprising the compositions of matter of the invention in a pharmaceutically acceptable carrier.

Thus, in a first aspect the invention provides compositions of matter for targeting biologically active compounds to phagocytic cells. In a second aspect, the invention provides compositions of matter and methods for the specific release of biologically active compounds inside phagocytic cells. The invention in yet a third aspect provides methods and compositions for intracellular delivery of targeted biologically active compounds to phagocytic cells. The invention also provides for organelle-specific intracellular targeting of biologically active compounds, specifically to phagolysosomes. In this aspect of the invention are also provided compositions and methods for organelle specific intracellular targeting using polar lipid moiety-linked compounds. In each of these aspects is provided methods and compounds for introducing biologically active compounds into phagocytic mammalian cells wherein the unconjugated compound would not otherwise enter said phagocytic cell. In this aspect is included the introduction of said biologically active compounds in chemical embodiments that would not otherwise enter the cell, for example, as phosphorylated embodiments. In yet another aspect is provided methods and compositions for the specific coordinate targeting of more than one biologically active compound to a specific cell type, that is, phagocytic mammalian cells. In another aspect, the invention provides reagents and compositions for introduction and specific release of antiviral or antimicrobial drugs or agents and other biologically-active compounds into cells infected by a pathological microorganism. In a final aspect, the invention provides methods and reagents for delayed, sustained or controlled intracellular release of biologically active compounds impregnated within a coated, porous microparticle, or coated onto a nonporous microparticle, wherein the degradation of either the coating or the microparticle or both provides said delayed, sustained or controlled intracellular release of the biologically active compound of the invention.

Specific preferred embodiments of the present invention will become evident from the following more detailed description of certain preferred embodiments and the claims.

DETAILED DESCRIPTION OF THE PREFERRED EMBODIMENTS

Figure 1:
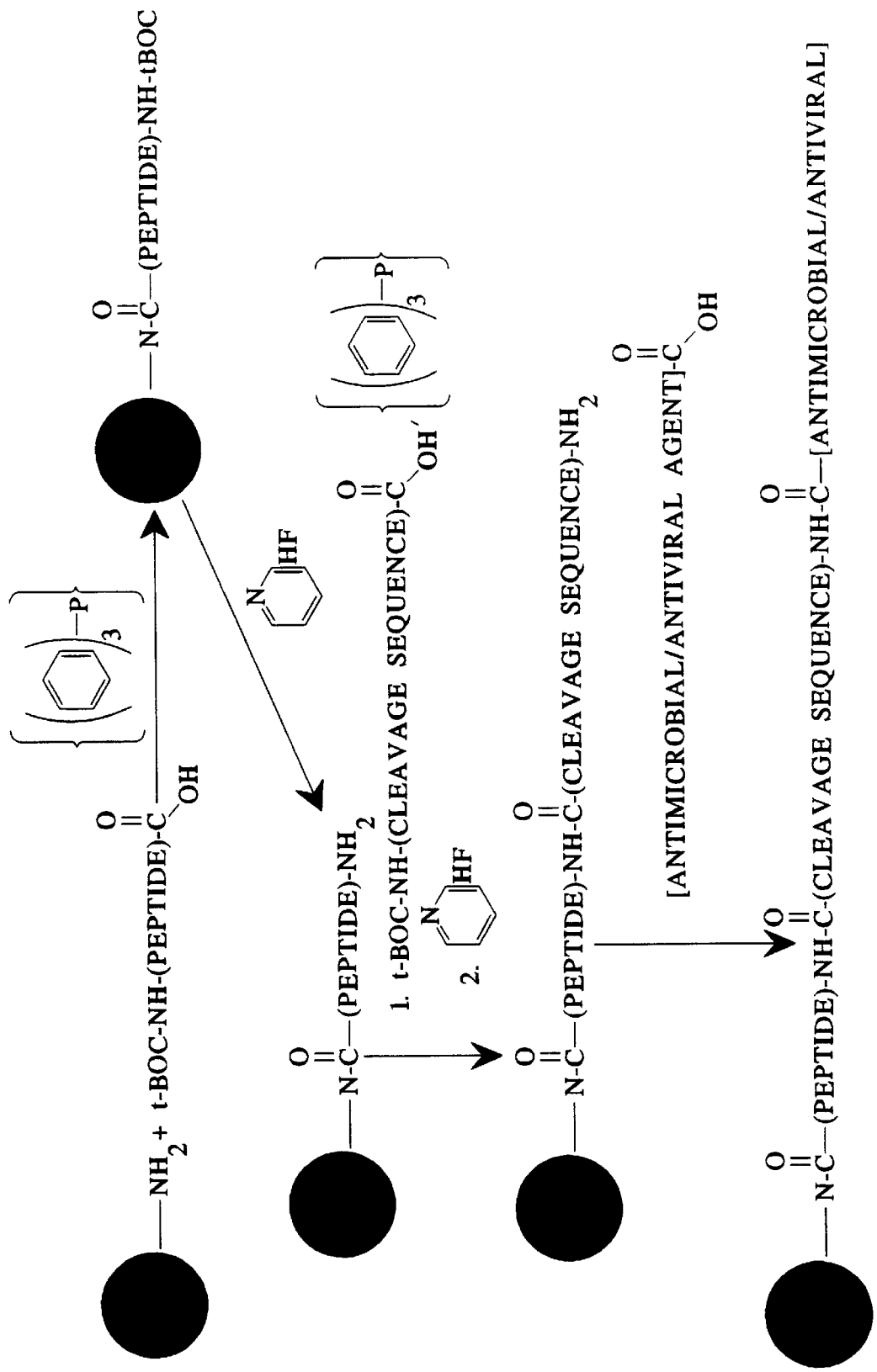
FIG. 1 depicts the synthetic scheme put forth in Example 1.

The present invention provides compositions of matter and methods for facilitating the entry biologically-active compounds into phagocytic cells. For the purposes of this invention, the term "biologically-active compound" is intended to encompass all naturally-occurring or synthetic compounds capable of eliciting a biological response or having an effect, either beneficial or cytotoxic, on biological systems, particularly cells and cellular organelles. These compounds are intended to include but are not limited to all varieties of drugs or agents, particularly antimicrobial drugs, defined herein to include antiviral, antibacterial, fungicidal and anti-protozoal, especially anti-plasmodial drugs, as well as peptides including antimicrobial peptides. Also included in the definition of "biologically active compounds" are antineoplastic drugs, particularly methotrexate and 5-fluorouracil and other antineoplastic drugs.

This invention provides microparticle-linked antiviral and antimicrobial agents for specific cell targeting to phagocytic mammalian cells. As used herein, phagocytic mammalian cells include but are not limited to monocytes, macrophages, alveolar macrophages, peritoneal macrophages, Kuppfer cells of the liver, macrophage cells resident in the central nervous system and the skin, all tissue inflammatory and noninflammatory macrophages, and phagocytic bone marrow cells.

This invention provides microparticle-linked antimicrobial agents wherein an antiviral or antimicrobial drug is linked to a microparticle via a cleavable linker moiety. The term "antimicrobial drug" is intended to encompass any pharmacological agent effective in inhibiting, attenuating, combating or overcoming infection of phagocytic mammalian cells by a microbial pathogen in vivo or in vitro. Antimicrobial drugs as provided as components of the antimicrobial agents of the invention include but are not limited to penicillin and drugs of the penicillin family of antimicrobial drugs, including but not limited to penicillin-G, penicillin-V, phenethicillin, ampicillin, amoxacillin, cyclacillin, bacampicillin, hetacillin, cloxacillin, dicloxacillin, methicillin, nafcillin, oxacillin, azlocillin, carbenicillin, mezlocillin, piperacillin, ticaricillin, and imipenim; cephalosporin and drugs of the cephalosporin family, including but not limited to cefadroxil, cefazolin, caphalexn, cephalothin, cephapirin, cephradine, cefaclor, cefamandole, cefonicid, cefoxin, cefuroxime, ceforanide, cefotetan, cefinetazole, cefoperazone, cefotaxime, ceftizoxime, ceftizone, moxalactam, ceftazidime, and cefixime; aminoglycoside drugs and drugs of the aminoglycoside family, including but not limited to streptomycin, neomycin, kanamycin, gentamycin, tobramycin, amikacin, and netilmicin; macrolide and drugs of the macrolide family, exemplified by azithromycin, clarithromycin, roxithromycin, erythromycin, lincomycin, and clindamycin; tetracyclin and drugs of the tetracyclin family, for example, tetracyclin, oxytetracyclin, democlocyclin, methacyclin, doxycyclin, and minocyclin; quinoline and quinoline-like drugs, such as, for example, naladixic acid, cinoxacin, norfloxacin, ciprofloxacin, ofloxicin, enoxacin, and pefloxacin; antimicrobial peptides, including but not limited to polymixin B, colistin, and bacatracin, as well as other antimicrobial peptides such as defensins (Lehrer et al., 1991, *Cell* 64:229–230), magainins (Zasloff, 1987, *Proc. Natl. Acad. Sci. USA* 84:5449–5453), cecropins (Lee et al., 1989, *Proc. Natl. Acad. Sci. USA* 86:9159 . 9162 and Boman et al., 1990, *Eur. J. Biochem.* 201:23–31), and others, provided as naturally-occurring or as the result of engineering to make such peptides resistant to the action of pathogen-specific proteases and other deactivating enzymes; other antimicrobial drugs, including chloramphenicol, vancomycin, rifampicin, metronidazole, ethambutol, pyrazinamide, sulfonamides, isoniazid, and erythromycin. Antiviral drugs, including but not limited to acyclovir, gangcyclovir, azidothymidine, cytidine arabinoside, ribavirin, amantadine, iododeoxyuridine, poscarnet, and trifluridine are also encompassed by this definition and are expressly included therein.

The invention also provides microparticle-linked antimicrobial agents wherein an antimicrobial agent is a toxin capable of specific cytotoxicity against the microbe, its host cell or both. The term "toxin" is intended to encompass any pharmacological agent capable of such toxicity, including for example ricin from jack bean, diphtheria toxin, and other naturally-occurring and man-made toxins.

In the antimicrobial agents as provided by this invention, said antimicrobial drugs or agents are linked to microparticles that are specifically phagocytized by phagocytic mammalian cells. It is an advantage of the present invention that antiviral and antimicrobial drugs or agents are specifically targeted to phagocytic mammalian cells, including, inter alia, monocytes and macrophages as provided further below, by attachment to the microparticles that are a component of the antimicrobial agents of the invention. The term "microparticle" as used herein is intended to encompass any particulate bead, sphere, particle or carrier, whether biodegradable or nonbiodegradable, comprised of naturally-occurring or synthetic, organic or inorganic materials, that is specifically phagocytized by phagocytic mammalian cells.

In one embodiment of the antiviral and antimicrobial agents of the invention, said microparticle is a porous particle having a defined degree of porosity and comprised of pores having a defined size range, wherein the antiviral or antimicrobial drugs or agents are impregnated within the pores of the microparticle. In such embodiments, a chemically or enzymatically-degradable coating covers the surface or outside extent of the microparticle, wherein the coating is specifically chemically or enzymatically degraded within the particular infected phagocytic cell after phagocytosis.

In a second embodiment of the invention, the microparticle is either a porous or a nonporous particle. In such embodiments, the surface or outside extent of the microparticle comprises chemically functional groups that form covalent linkages with the antiviral or antimicrobial drug component of the antimicrobial agents of the invention, preferably via a chemically or enzymatically cleavable linker moiety. In such embodiments, the cleavable linked moiety is specifically chemically or enzymatically cleaved within the particular infected phagocytic cell after phagocytosis.

In a third embodiment of the invention, the microparticle is nonporous and the antiviral or antimicrobial drug is coated on the outside of the microparticle, the microparticle further coated with an organic coating material to control the specific release of the antiviral or antimicrobial drug in infected cells. In such embodiments, a chemically or enzymatically-degradable coating covers the surface or outside extent of the microparticle, wherein the coating is specifically chemically or enzymatically degraded within the particular infected phagocytic cell after phagocytosis.

The microparticle component of the antiviral or antimicrobial agents of the invention include any particulate bead, sphere, particle or carrier having a diameter of about 1 to about 1000 nanometers (about 0.001–1 µm). The microparticles of the invention are provided comprised of polystyrene, cellulose, silica, and various polysaccharides including dextran, agarose, cellulose and modified, crosslinked and derivatized embodiments thereof. Specific examples of the microparticles of the invention include polystyrene, cellulose, dextran crosslinked with epichlorohydrin (Sephadex™, Pharmacia, Uppsala, Sweden), polyacrylamide crosslinked with bisacrylamide (Biogel™, BioRad, USA), agar, glass beads and latex beads. Derivatized microparticles include microparticles derivatized with carboxyalkyl groups such as carboxymethyl, phosphoryl and substituted phosphoryl groups, sulfate, sulfhydryl and sulfonyl groups, and amino and substituted amino groups.

In the antimicrobial agents of the invention as provided in one aspect, the microparticles and antiviral and antimicrobial drugs or agents are linked via a chemically or enzymatically cleavable linker moiety. In another aspect of the antimicrobial agents of the invention, the antiviral and antimicrobial drugs or agents are impregnated within porous microparticles coated with a chemically or enzymatically degradable coating. In another aspect of the antimicrobial agents of the invention, antiviral or antimicrobial drugs or agents coat the external surface of a nonporous microparticle, which is thereafter further coated with a chemically or enzymatically degradable coating. In all aspects, specific release of the antiviral or antimicrobial drug is dependent on specific chemical or enzymatic cleavage of the coating or linker moieties inside infected phagocytic cells after phagocytosis of the antimicrobial agent. The specificity of the cleavage of the linker or coating moieties as provided by this invention is the result of the combination of particular linker or coating moieties which are selected to be specifically cleaved inside the infected phagocytic cell. In one aspect, such specific cleavage is due to an chemical linkage which is labile within the infected phagocytic cell due to conditions caused by or that result from infection of the phagocytic cell with a particular microbial pathogen. In another aspect, such specific cleavage is due to an enzymatic activity which is produced either by the microbial pathogen itself or by the phagocytic cell as the result of infection with said microbial pathogen, wherein the linkage is enzymatically cleaved by the enzymatic activity.

Examples of such combinations resulting in specific release of the antiviral or antimicrobial drug component of the antimicrobial agents of the invention within infected phagocytic cells include but are not limited to a urea-based linker for use against a pathogen which produces urease (e.g., *Mycobacteria spp.* and *B. pertussis*); a peptide linker comprised of (AlaAlaAlaAla)$_n$, wherein n can be an integer from 1–5, for use against a pathogen that produces the protease oligopeptidase A (e.g., *Salmonella spp.*); a peptide comprised of from 3 to about 20 amino acids comprising the sequence —Pro—Xaa—Pro—, where Xaa is any amino acid, for use against a pathogen that produced proline peptidase (e.g., *Salmonella spp.*); peptides comprising the dipeptide MetMet or LeuAla, or peptides comprising the amino acid sequence GSHLVEAL, HLVRALYL, VEALYLVC, or EALYLVCG, for use against human immunodeficiency virus 1 producing a specific protease termed HIV-1 protease; a peptide comprising the amino acid sequence: —Ala—Xaa—Cys$_{Acm}$—Tyr—Cys—Arg—Ile—Pro—Ala—Cys$_{Acm}$—Ile—Ala—Gly—Asp—Arg—Arg—Tyr—Gly—Thr—Cys$_{Acm}$—Ile—Tyr—Gln—Gly—Arg—Leu—Trp—Ala—Phe—Cys$_{Acm}$—Cys$_{Acm}$—, wherein the microbial pathogen expresses an enzymatic activity that specifically disables the endogenous antimicrobial peptide defensin (e.g., *Mycobacterium spp.* and *L. pneumophila*), (—Cys$_{Acm}$—) represent cysteine residues having the side chain sulfur atom protected by covalent linkage to an acetamidomethyl group (it will be recognized that embodiments of such peptides having alternative sulfur protecting groups are also within the scope of the disclosure herein) and Xaa is either absent or Asp; said peptides are also useful as components of the microparticulate antimicrobial compounds of the invention against a pathogen such as *Legionella spp.* producing a 39 kDa metalloprotease; hippurate esters that are hydrolyzed by pathogen-specific (e.g., *L. pneumophila* and *Listeria spp.*) hydrolase; nicotinic acid amides cleaved by nicotinamidases, pyrazinamides cleaved by pyrazinamidase; allolactose linkages cleaved by β-galactosidase; and allantoate linkages cleaved by allantoicase (e.g., *Mycobacterium spp.*).

In certain specific embodiments, combinations or mixtures of the antimicrobial agents of the invention will comprise the therapeutic pharmaceutical agents of the invention, as provided below. In other embodiments, said mixtures will include compositions of matter comprising a microparticle covalently linked to an enzyme having an activity that recognizes and cleaves the linker or coating moiety of the other antimicrobial agent component of the mixture, said enzyme-linked microparticles having activity as drug release accelerators.

In yet further embodiments of the antimicrobial agents of the invention, said antimicrobial agents are optionally comprised of a polar lipid targeting moiety comprised of one or a plurality of polar lipid molecules. The polar lipid moiety in such embodiments is covalently linked to either the antiviral or antimicrobial drug or to both the antiviral or antimicrobial drug and the cleavable linker moiety. The polar lipid moiety is linked to the antiviral or antimicrobial drug through an organic spacer moiety comprising a first functional linker group and a second functional linker group. The term "polar lipid moiety" as defined herein is intended to mean any polar lipid having an affinity for, or capable of crossing, a biological membrane. Polar lipid moieties comprising said embodiments of the invention include but are not limited to acyl carnitine, acylated carnitine, sphingosine, ceramide, phosphatidyl choline, phosphatidyl glycerol, phosphatidyl ethanolamine, phosphatidyl inositol, phosphatidyl serine, cardiolipin, phosphatidic acid, sphingomyelin and other sphingolipids, as these terms are understood in the art (see, Lehninger, *Biochemistry,* 2d ed., Chapters 11 & 24, Worth Publishers: New York, 1975).

These embodiments of the invention may be further comprised of an organic spacer moiety comprising a first end and a second end, each end of the spacer having a functional linking group. For the purposes of this invention, the term "organic spacer" or "organic spacer moiety" is intended to encompass any chemical entity that links a biologically-active compound such as an antiviral or antimicrobial drug and a polar lipid moiety. Such organic spacer moieties may be designed to facilitate, influence, modulate or regulate the release of the biologically-active compound at a desired intracellular target site. Such organic spacers may also facilitate enzymatic release at certain intracellular sites. Functional organic spacer groups, as described herein, include, but are not limited to aminohexanoic acid, polyglycine, polyamides, polyethylenes, and short functionalized polymers having a carbon backbone which is from one to about twelve carbon molecules in length. Particularly preferred embodiments of such spacer moieties comprise peptides of formula (amino acid)n, wherein n is an integer between 2 and 100 and the peptide is a polymer of one or more amino acids.

As used herein, the term "linker functional group" is defined as any functional group for covalently linking the polar lipid moiety or biologically-active agent to the organic spacer group. This definition also includes functional groups comprising a biologically active compound or a microparticle or both covalently linking the biologically active compound or the microparticle to a cleavable linker moiety.

Linker functional groups can be designated either "weak" or "strong" based on the stability of the covalent bond which the linker functional group will form. The weak functionalities include, but are not limited to phosphoramide, phosphoester, carbonate, amide, carboxyl-phosphoryl anhydride, ester and thioester. The strong functionalities include, but are not limited to ether, thioether, amine, amide and ester. Strong linker functional groups comprise the functional covalent linkages between the microparticles, the biologically active compounds and the cleavable linker moieties of the invention. Strong linker functional groups between the organic spacer group and the biologically-active compound will tend to decrease the rate at which the compound will be released at an intracellular target site, whereas the use of a weak linker functional group between the organic spacer moiety and the compound may act to facilitate release of the compound at the intracellular target site. Enzymatic release is also possible, but such enzyme-mediated modes of release will not necessarily be correlated with bond strength in such embodiments of the invention. Organic spacer moieties comprising enzyme active site recognition groups, such as spacer groups comprising peptides having proteolytic cleavage sites therein, are envisioned as being within the scope of the present invention.

The antimicrobial agents of this invention are useful in inhibiting, attenuating, arresting, combating and overcoming infection of phagocytic mammalian cells with pathogenic microorganisms in vivo and in vitro. To this end, the antimicrobial agents of the invention are administered to an animal infected with a pathogenic microorganism acutely or chronically infecting phagocytic mammalian cells. The antimicrobial agents of the invention for this use are administered in a dosage and using a therapeutic protocol sufficient to have an antimicrobial effect in the phagocytic cells of the animal. Thus, methods of treating microbial infections in a mammal, specifically infections of phagocytic mammalian cells, are provided. Pharmaceutical compositions useful in the methods provided by the invention are also provided.

The following Examples illustrate certain aspects of the above-described method and advantageous results. The following examples are shown by way of illustration and not by way of limitation.

EXAMPLE 1

An antimicrobial agent is prepared by conjugating a specifically-cleavable peptide to a derivatized microparticle as follows. An derivatized microparticle comprising unconjugated amino groups is reacted with a proteolytically-inert peptide in which the terminal amine and any of the constituent amino acid side chain reactive amines are covered by tert-butoxycarbonyl (t-Boc) protecting groups in the presence of triphenyl phosphine as described by Kishimoto (1975, Chem. Phys. Lipids 15:33–36). The peptide/microparticle conjugate is then reacted in the presence of pyridine hydrofluoride as described by Matsuura et al. (1976, J. Chem. Soc. Chem. Comm. xx: 451–459) to remove the t-Boc protecting groups. The peptide/microparticle is then conjugated to the specifically-cleavable peptide, in which the terminal amine and any of the constituent amino acid side chain reactive amines are covered by t-Boc protecting groups, as described in the presence of triphenyl phosphine. After deprotection of reactive amines with pyridine hydrofluoride as described, an antimicrobial drug having a reactive carboxylic acid group is conjugated to a free amino group of the microparticle/peptide/specifically-cleavable peptide to yield the antimicrobial agent of the invention. This reaction scheme is illustrated in FIG. 1.

EXAMPLE 2

Figure 2:
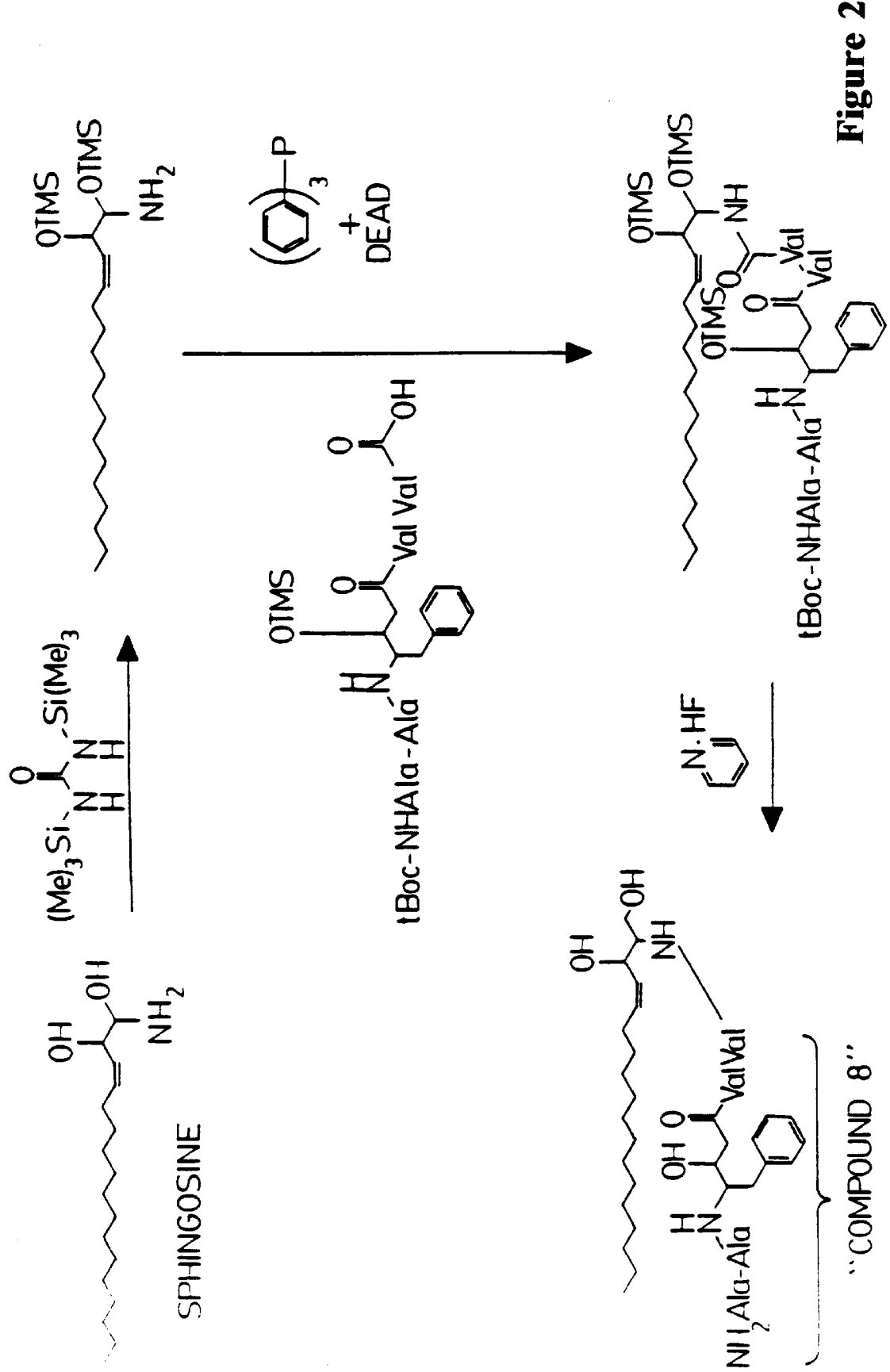
FIG. 2 depicts the synthetic scheme put forth in Example 2.

An antiviral compound (HIV1 protease inhibitor; compound 8) is conjugated to sphingosine as follows. Sphingosine is reacted with 1,3 bis(trimethylsilyl)urea as described by Verbloom et al. (1981, Synthesis 1032:807–809) to give a trimethylsilyl derivative of sphingosine. The sphingosine derivative is then conjugated with the antigenically-active peptide in which the terminal amine and any of the constituent amino acid side chain reactive amines are covered by tert-butoxycarbonyl (t-Boc) protecting groups in the presence of diethylazo-dicarboxylate (DEAD) and triphenyl phosphine as described by Kishimoto (1975, Chem. Phys. Lipids 15:33–36). The sphingosine/peptide conjugate is then reacted in the presence of pyridine hydrofluoride as described by Matsuura et al. (1976, J. Chem. Soc. Chem. Comm. xx:451–459) to remove the t-Boc protecting group, to yield the antigenically-active peptide covalently linked to sphingosine through an amide bond. This reaction scheme is illustrated in FIG. 2. Sphingosine/drug conjugates are then linked to microparticles as described in Example 1.

EXAMPLE 3

Figure 3A:
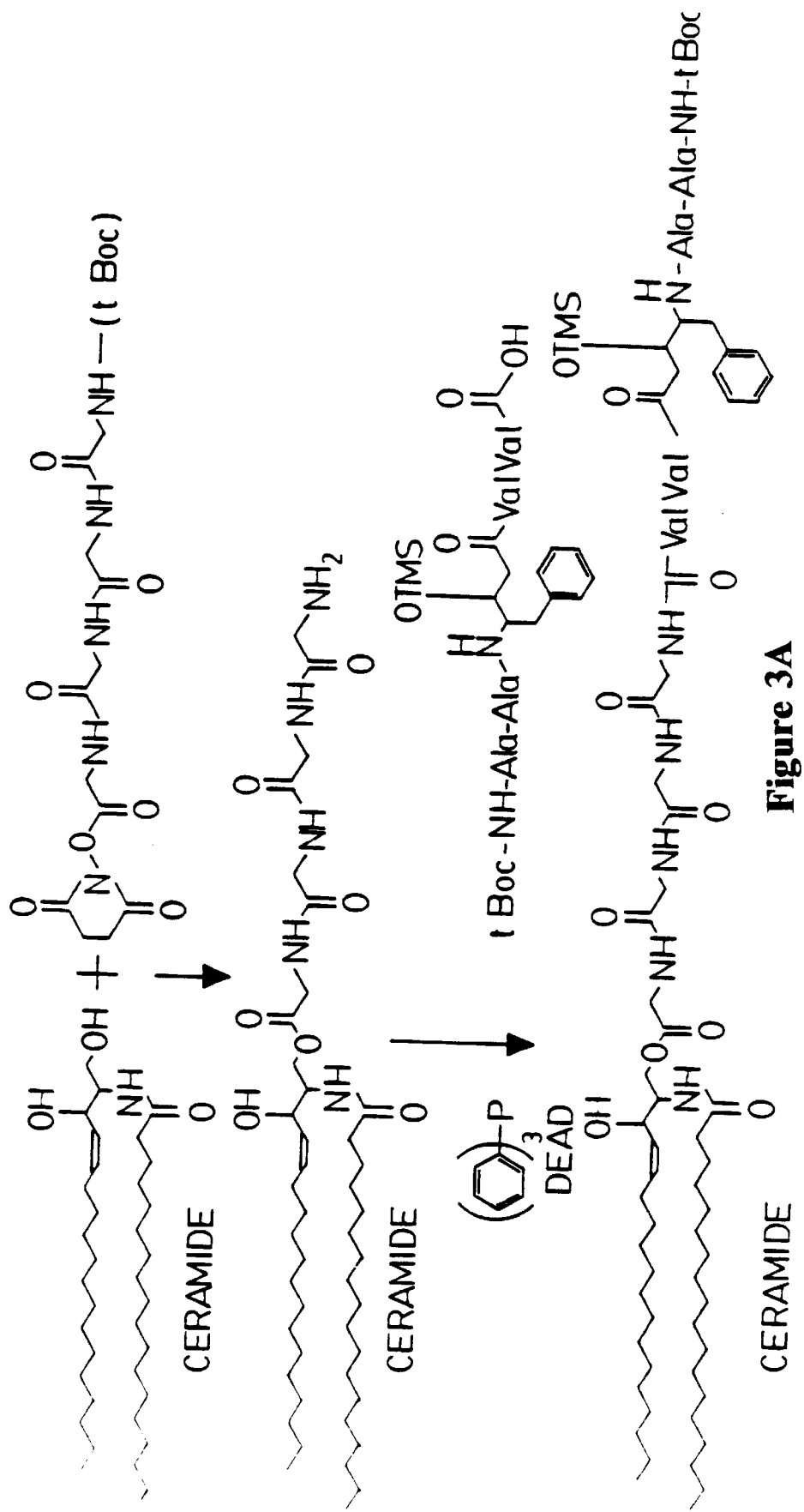
FIGS. 3A–3B depict the synthetic scheme put forth in Example 3.
Figure 3B:
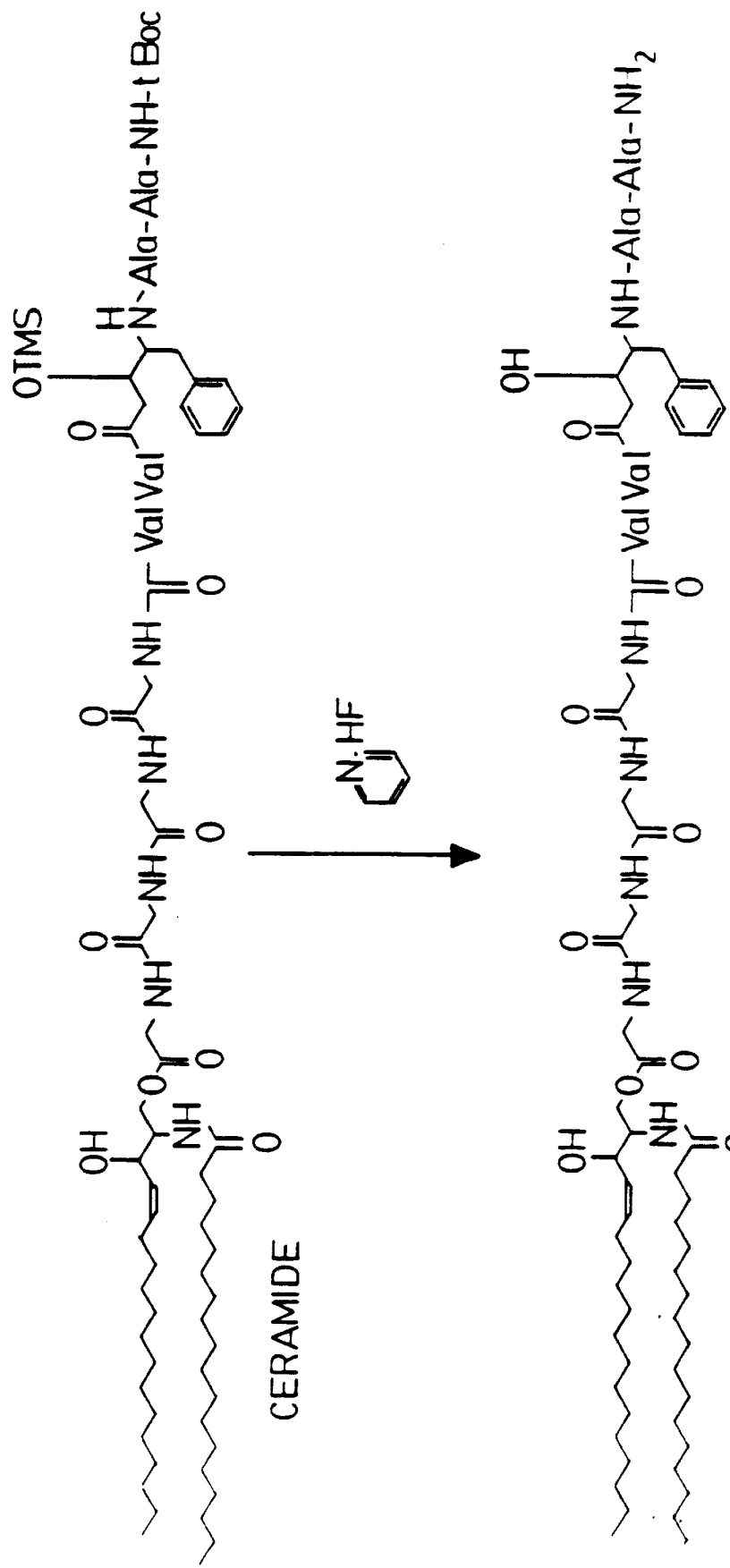

An antiviral compound (compound 8) is conjugated to ceramide via a polyglycine spacer as follows and as illustrated in FIG. 3. The amino terminus of polyglycine is protected by a t-Boc group. Polyglycine is conjugated through its carboxy terminus to ceramide forming an ester linkage, as described in Anderson et al., ibid. The resulting compound is then conjugated through the amino terminus of the polyglycine residue. The amino terminus of Compound 8 is also protected by a t-Boc protecting group. Conjugation with polyglycyl-sphingosine takes place between the amino terminus of the polyglycyl spacer moiety and the carboxy terminus of the HIV-1 protease inhibitor. This reaction is carried out in the presence of DEAD and triphenyl phosphine as described in Examples 1 and 2. Following this conjugation, the amino terminus of the HIV-1 protease inhibitor residue is deprotected according to the method of Matsuura et al., ibid. Ceramide/drug conjugates are then linked to microparticles as described in Example 1.

EXAMPLE 4

Figure 4:
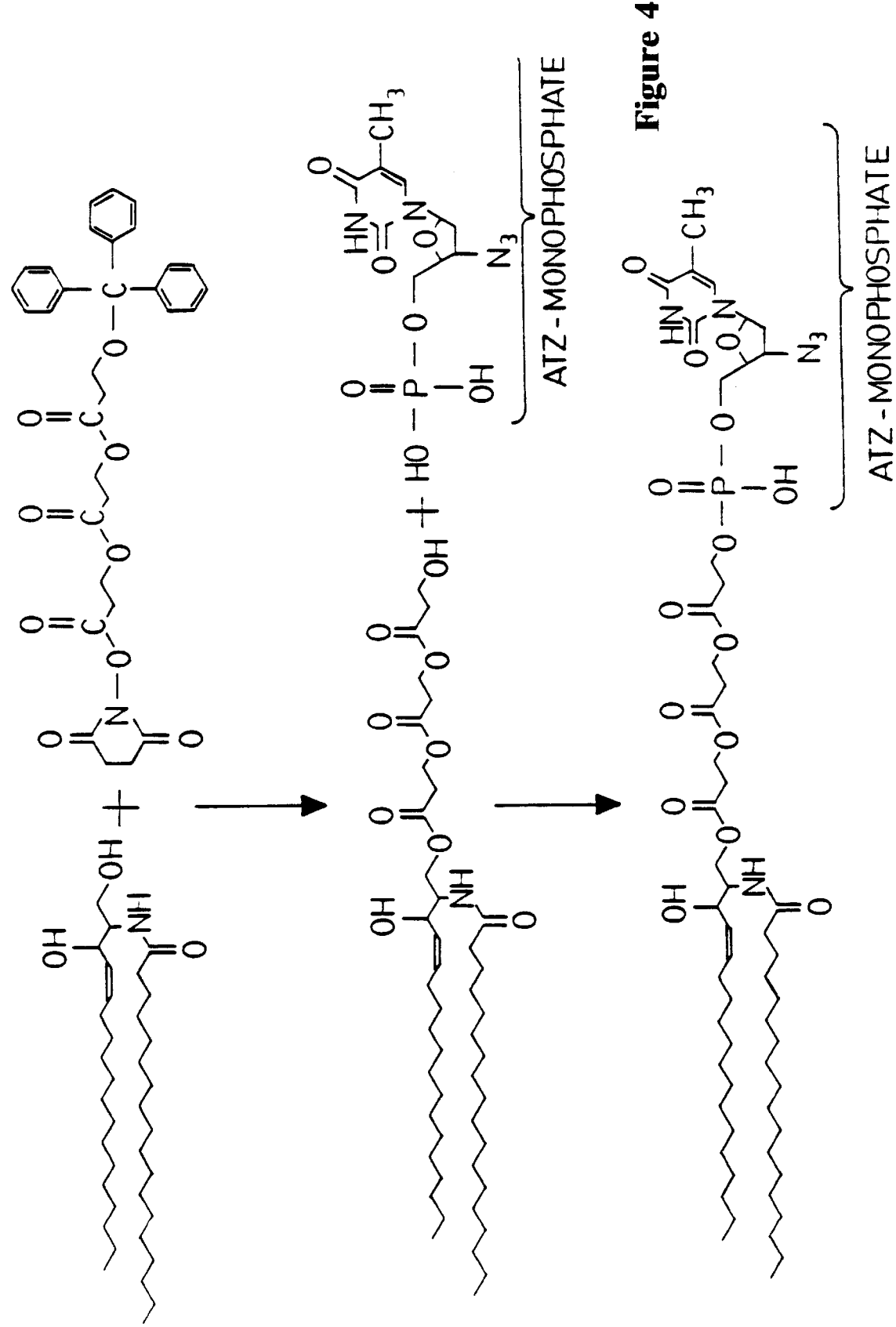
FIG. 4 depicts the synthetic scheme put forth in Example 4.

An antiviral compound is prepared wherein ceramide is first conjugated to a first end of an oligomeric 3-hydroxy propanoic acid spacer through an ester functional group, and wherein AZT is conjugated to a second end of said polyester spacer through a phosphodiester bond. First a polyester spacer is obtained, having a carboxyl at a first end and a triphenylmethyl group esterified to a second end. This spacer is conjugated to ceramide at its first end through an ester functional linker group according to the method of Anderson et al., ibid. This compound is then conjugated through the second end of the spacer compound to AZT monophosphate by means of a phosphodiester bond according to the method of Baer (1955, Can. J. Biochem. Phys. 34:288). In this antiviral compound, the bond breakage between the spacer and the drug would be slow in the absence of a phosphohydrolase. This reaction scheme is illustrated in FIG. 4. Ceramide/drug conjugates are then linked to microparticles as described in Example 1.

EXAMPLE 5

Figure 5:
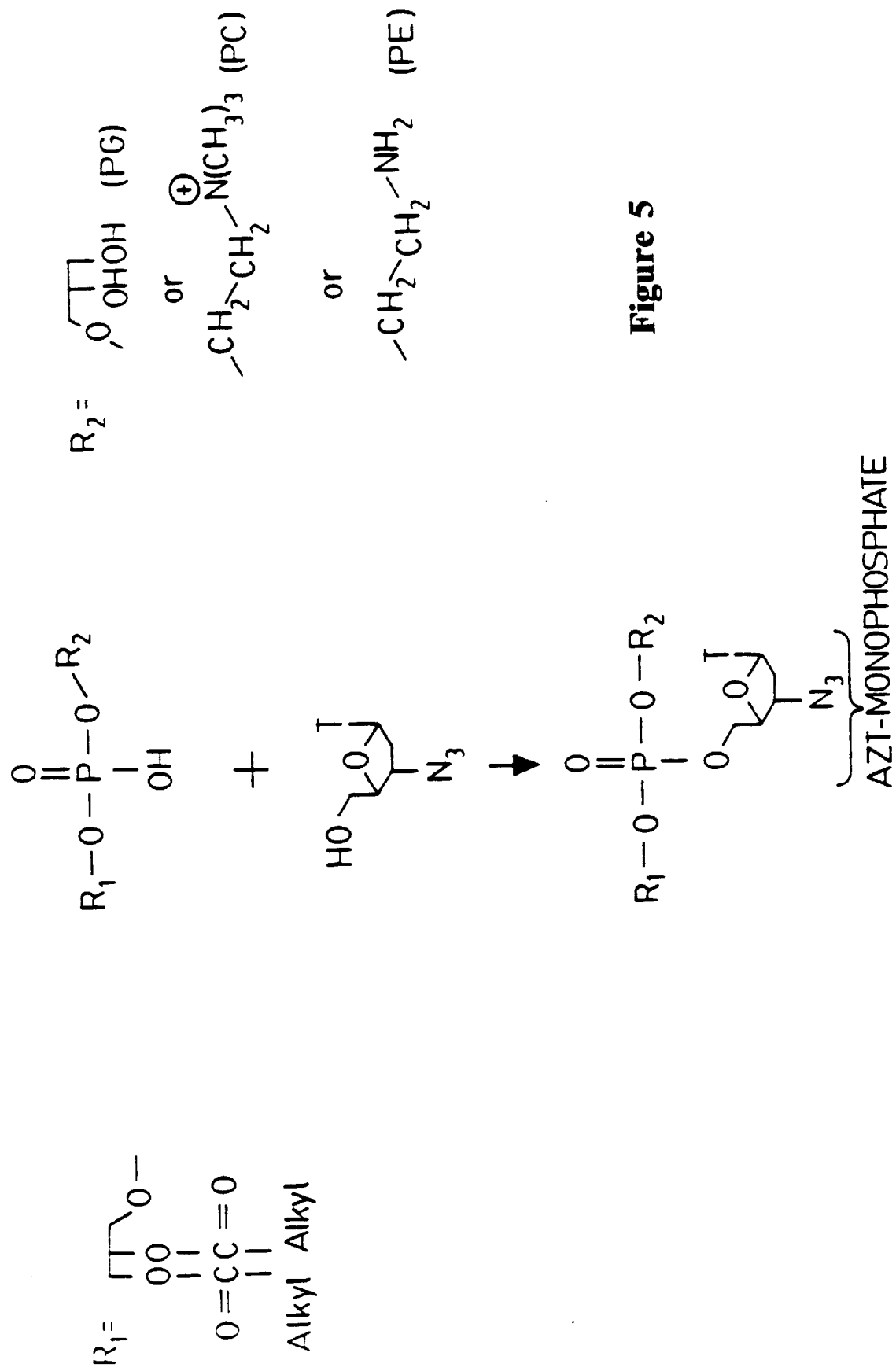
FIG. 5 depicts the synthetic scheme put forth in Example 5.

An antiviral compound wherein phosphatidic acid, phosphatidyl choline, phosphatidyl serine, phosphatidyl inositol, phosphatidyl glycerol or phosphatidylethanolamine is linked through a phosphoester linker functional group to the antiviral drug azidothymidine (AZT). Phosphatidic acid, phosphatidyl choline, phosphatidyl serine, phosphatidyl inositol, phosphatidyl glycerol or phosphatidyl ethanolamine is conjugated to AZT according to the method of Salord et al. (1986, Biochim. Biophys. Acta 886:64–75). This reaction scheme is illustrated in FIG. 5. Phospholipid/drug conjugates are then linked to microparticles as described in Example 1.

EXAMPLE 6

Figure 6:
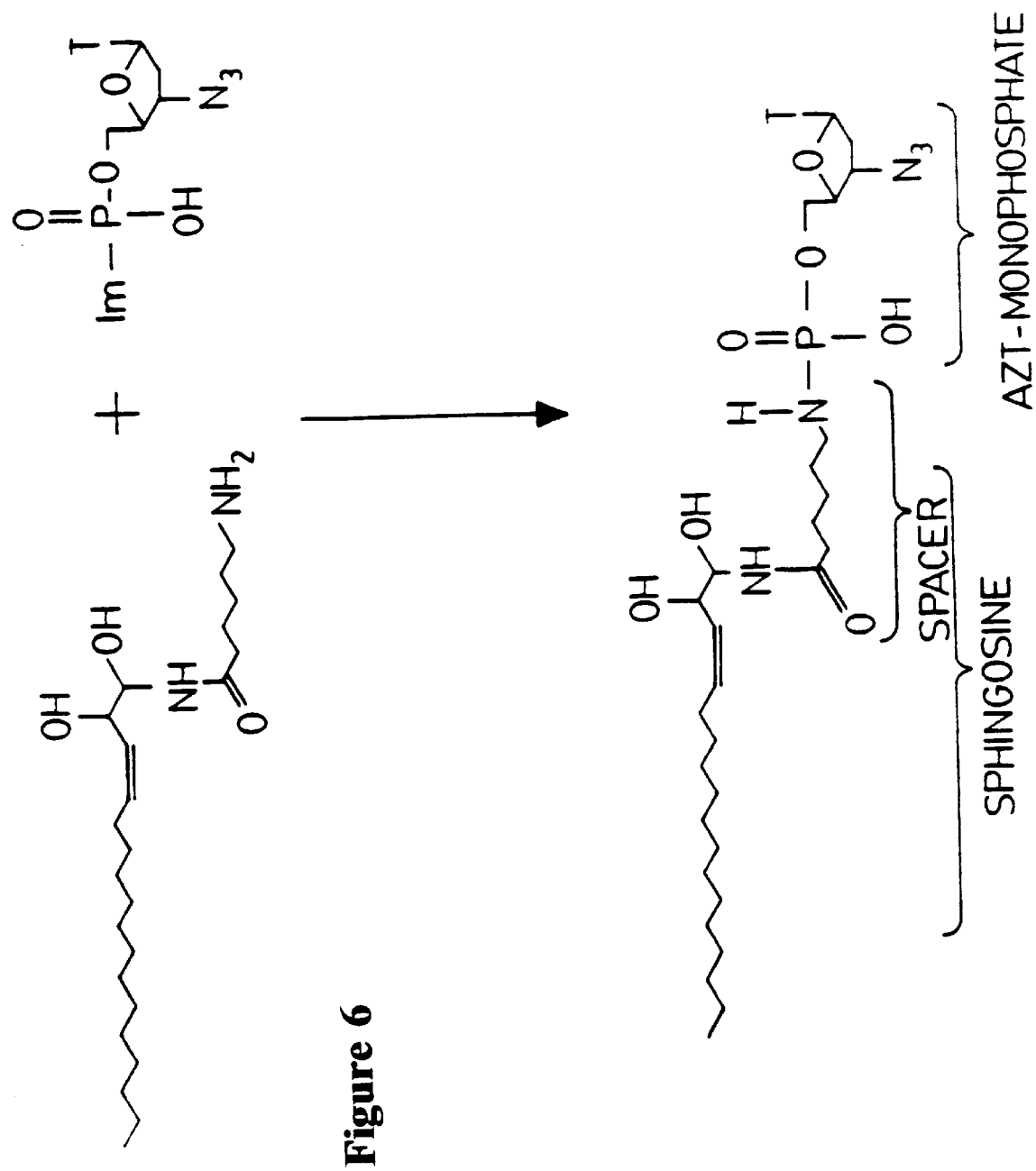
FIG. 6 depicts the synthetic scheme put forth in Example 6.

An antiviral compound is prepared wherein aminohexanoyl sphingosine is conjugated to AZT. Aminohexanoyl sphingosine is conjugated with AZT according to the method of Kishimoto (1975, Chem. Phys. Lipid 15:33–36). This reaction scheme is illustrated in FIG. 6 to yield aminohexanoyl sphingosine conjugated to AZT through a phosphoramide bond. Such conjugates are then linked to microparticles as described in Example 1.

EXAMPLE 7

Figure 7:
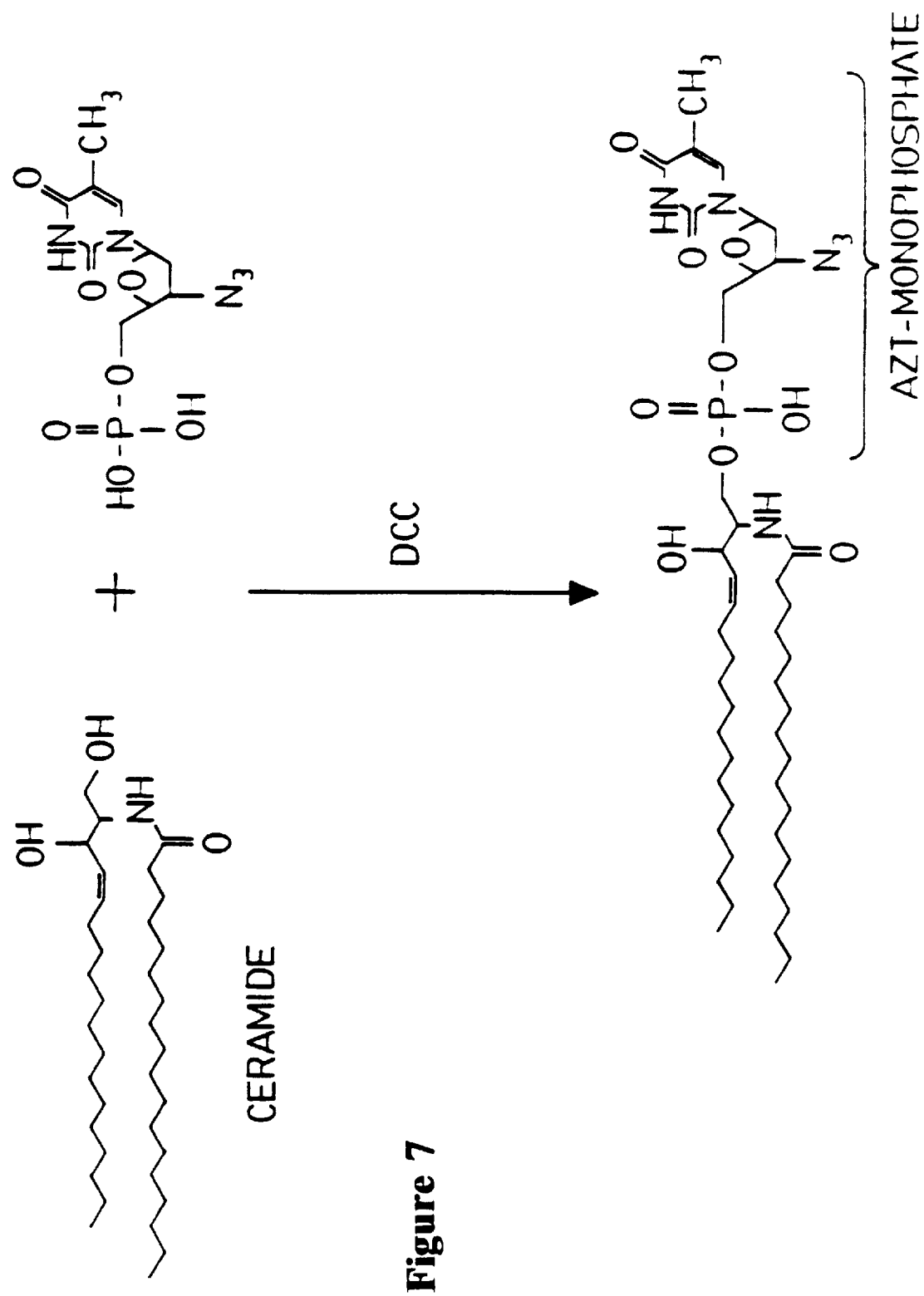
FIG. 7 depicts the synthetic scheme put forth in Example 7.

An antiviral compound consisting of ceramide conjugated to AZT-monophosphate is provided. Ceramide is reacted with AZT-monophosphate in the presence of dicyclohexylcarbodiimide as described in Smith and Khorana (1958, J. Amer. Chem. Soc. 80:1141) to yield ceramide conjugated through a phosphodiester bond to AZT-monophosphate. This reaction scheme is illustrated in FIG. 7. The AZT/polar lipid conjugate is then linked to a microparticle as described in Example 1.

EXAMPLE 8

Figure 8:
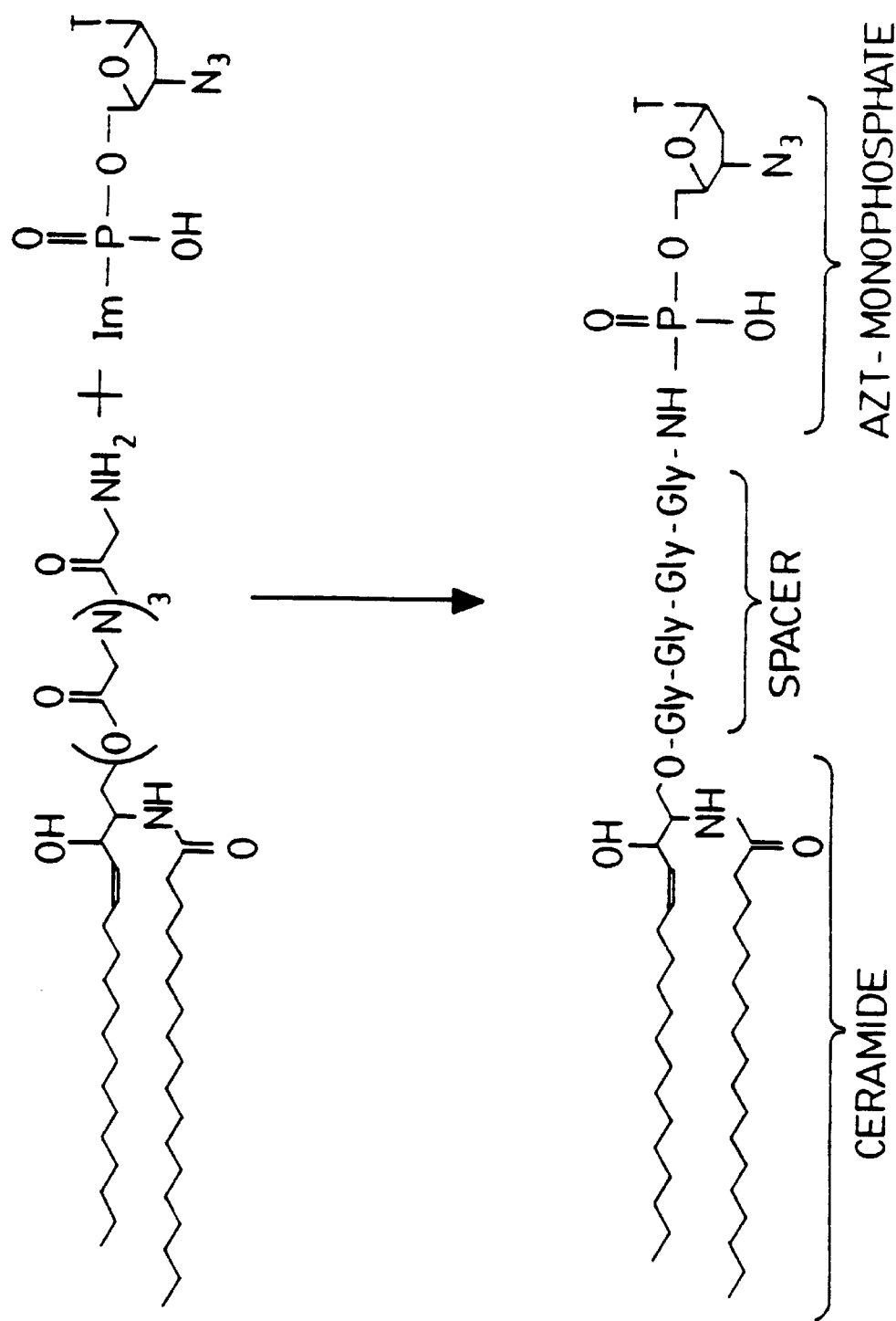
FIG. 8 depicts the synthetic scheme put forth in Example 8.

An antiviral compound is prepared wherein ceramide is conjugated through an ester functional group to a first end of a polyglycine spacer, and wherein AZT is conjugated through a phosphoester functional group to a second end of the polyglycine spacer. Ceramide is first conjugated through an ester functional group to a first end of a polyglycine spacer (as described in Example 2). The ceramide-polyglycine compound is then conjugated through a phosphoester bond to a second end of the polyglycine spacer to AZT monophosphate according to the method of Paul and Anderson, ibid. This reaction scheme is illustrated in FIG. 8. Conjugates as prepared herein are then linked to prepared microparticles as described in Example 1.

EXAMPLE 9

Figure 9A:
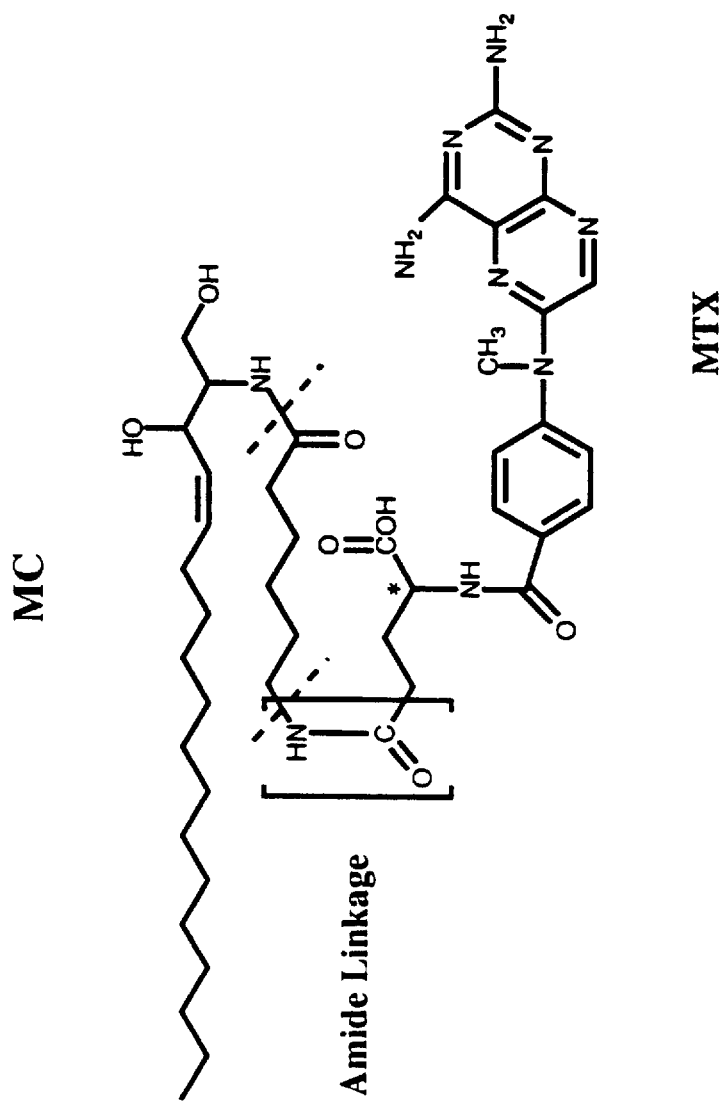
FIGS. 9A through 9D depict prodrugs tested as in Example 9.
Figure 9B:
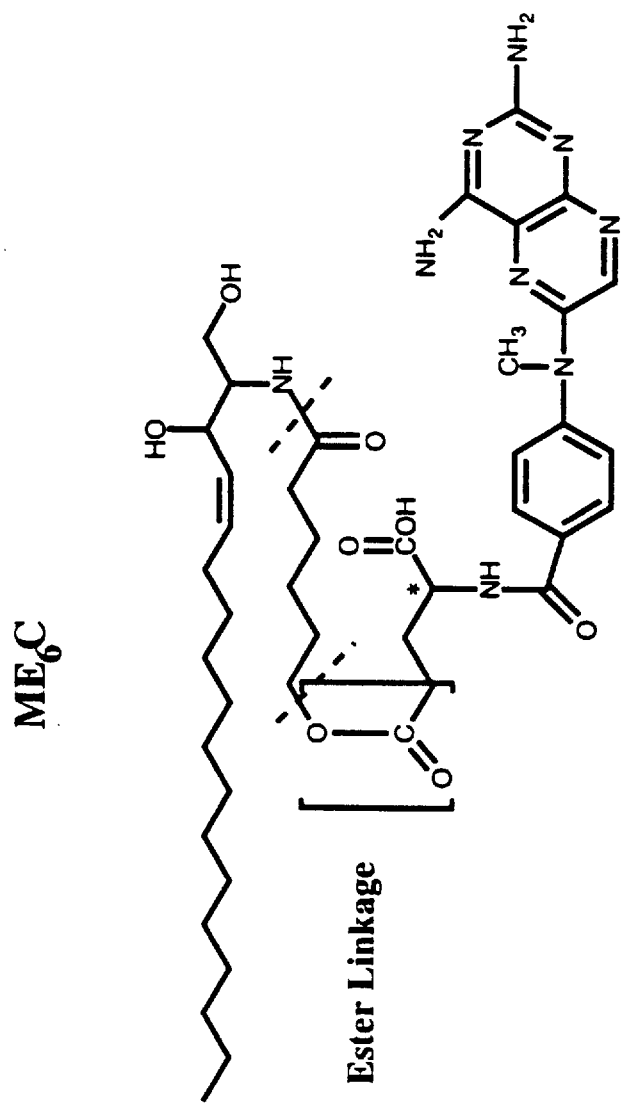
Figure 9C:
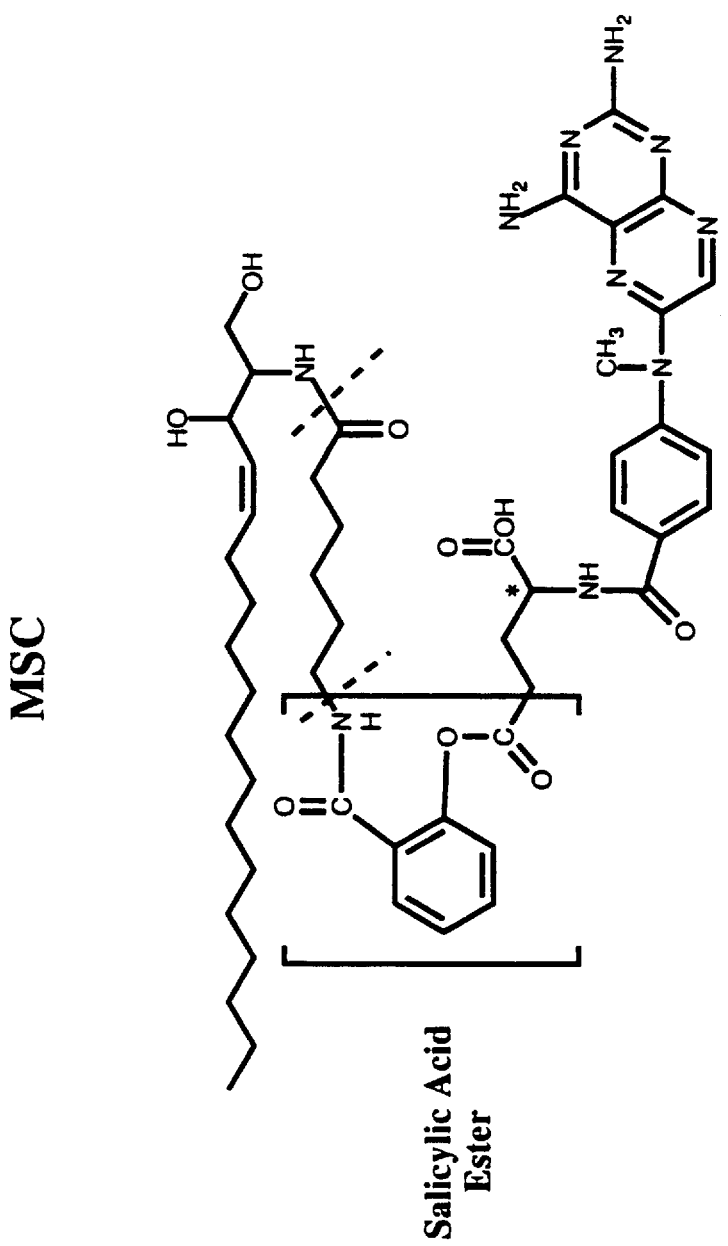
Figure 9D:
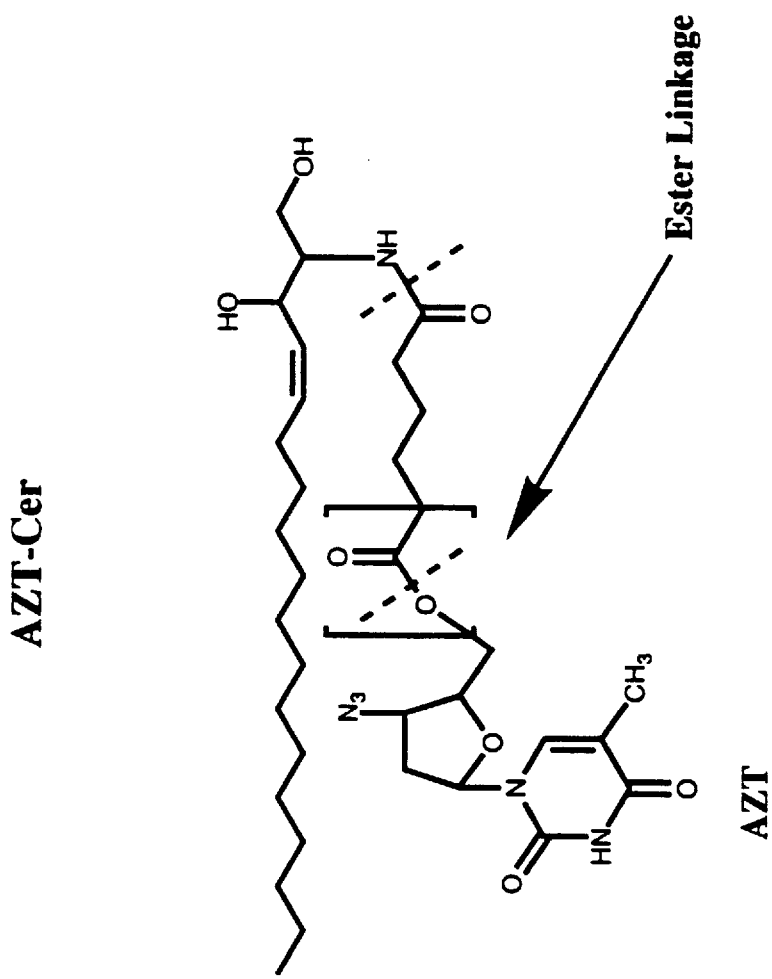

The effect of presenting a biologically active compound such as a drug to mammalian cells as a prodrug covalently linked to a polar lipid carrier moiety was determined as follows. The antifolate drug methotrexate was conjugated with a variety of polar lipid carriers via organic spacer moieties having specific reactive functional groups. A representative sample of such compounds is shown in FIGS. 9A through 9C, wherein MC represents Mtx linked to sphingosine via an amide bond to a 6-aminohexanoic acid spacer, $ME_6C$ represents Mtx linked to sphingosine via an ester linkage to a 6-hydroxyhexanoic acid spacer, and MSC represents Mtx linked to sphingosine via a salicylic acid ester linkage to a 6-aminohexanoic acid spacer. Also studied was a conjugate of azidothymidine linked to sphingosine via an ester linkage to a 6-hydroxyhexanoic acid spacer (N-AZT-ceramide). The compounds were tested for their growth inhibitory effects on murine NIH 3T3 cells growing in cell culture. About one million such cells per P100 tissue culture plate were grown in DMEM media supplemented with 10% fetal calf serum (GIBCO, Grand island, N.Y.) in the presence or absence of a growth-inhibitory equivalent of each prodrug. Cell numbers were determined after 70 hours growth in the presence or absence of the prodrug. In a second set of experiments was included in the growth media an amount of a brain homogenate containing an enzymatically-active esterase.

The results from these experiments are shown in Table I. As can be seen from these data, the MC prodrug had no effect on the growth and survival of the cells. This result did not change upon co-incubation with the esterase-containing brain extract, which was expected due to the nature of the drug/spacer linkage (an amide bond). A different result was obtained with the $ME_6C$ conjugate. The prodrug was ineffective in inhibiting cell growth or survival in the absence of brain extract. Upon addition of the brain extract, a significant increase in Mtx cytotoxicity was observed. This is consistent with cleavage of the ester linkage by the brain extract-derived esterase. A similar result was obtained with the MCS conjugate, indicating that the brain extract esterase activity was capable of cleaving the salicylic acid ester.

Table II shows the results of drug uptake studies performed with the prodrug N-AZT-ceramide. Antiviral amounts of the prodrug conjugate were added to NIH 3T3 cell cultures, and the antiviral activity of the prodrug was found to be equivalent to the activity of free AZT. In addition, upon removal of the prodrug, intracellular retention of prodrug was found to be up to 15-fold higher than free AZT (Table II) over a 23 h period.

These results indicate that for Mtx-containing conjugates, the free drug must be released from the prodrug for biological activity. These results suggest that specific release of this drug, and perhaps others, can be achieved using cleavable linker moieties that are specifically cleaved only in pathogen-infected cells.

TABLE I

| Sample[1] | # cells/plate[2] | Sample[3] | # cells/plate[4] |
|---|---|---|---|
| Control/FBS | $7.8 \times 10^6$ | Control/FBS | $13 \times 10^6$ |
| $ME_6C$/FBS | $6.5 \times 10^6$ | MSC/FBS | $2.1 \times 10^6$ |
| $ME_6C$/brain | $2.7 \times 10^6$ | MSC/brain | $0.51 \times 10^6$ |
| Mtx/FBS | $0.16 \times 10^6$ | Mtx/FBS | $0.13 \times 10^6$ |
| Mtx/brain | $0.09 \times 10^6$ | Mtx/brain | $0.06 \times 10^6$ |
| Control/brain | N.D. | Control/brain | $6.2 \times 10^6$ |

[1]cells incubated with drug/FBS or drug/brain extract for 1 hour at 37° C.
[2]cell growth and survival determined 70 hours after drug addition
[3]cells incubated with drug/FBS or drug/brain extract for 2 hours at 37° C.
[4]cell growth and survival determined 72 hours after drug addition

TABLE II

| Time[1] | AZT[2] | N-AZT-Ceremide[2] |
|---------|--------|-------------------|
| 0 hr.   | 6.49   | 8.45              |
| 23 hr.  | 0.55   | 7.78              |

[1]time between the end of drug treatment and assay for intracellular drug concentration
[2]nM/10⁶ cells

EXAMPLE 10

Antimicrobial agents of the invention are used as follows. The antimicrobial agent or a negative control (saline) are administered to an animal infected with a microbial pathogen using both optimal and suboptimal dosages and the most appropriate route of administration. After an optimal time period (determined from the nature of the infection), phagocytic cells are collected from the animal and tested for infection with the microbial pathogen. Phagocytic cells from peripheral blood are isolated using conventional methods (Ficoll-Hypaque density gradient centrifugation) and tested for the presence of infectious microbial pathogens using conventional immunological, microbiological and biochemical testing protocols (see *Laboratory Test Handbook*, Jacobs et al., eds., Lexi-Comp, Inc: Cleveland, Ohio, 1994; *Clinical Laboratory Medicine*, McClatchey, ed., Williams & Wiklins: Baltimore, Md., 1994; *Clinical Diagnosis and Management by Laboratory*, 18th Ed., J. B. Henry, ed., W. B. Saunders: Philadelphia, 1991).

It should be understood that the foregoing disclosure emphasizes certain specific embodiments of the invention and that all modifications or alternatives equivalent thereto are within the spirit and scope of the invention as set forth in the appended claims.

What is claimed is:

1. A composition of matter comprising a biologically-active compound, a nonporous microparticle, and an organic coating material, wherein the nonporous microparticle is coated with the biologically-active compound and said coated microparticle is further coated with the organic coating moiety, and wherein the organic coating material is specifically degraded inside a phagocytic mammalian cell infected with a microorganism to allow release of the biologically-active compound within the infected cell.

2. The composition of matter of claim 1 wherein the biologically-active compound is a peptide.

3. The composition of matter of claim 2 wherein the peptide is an antiviral peptide or an antimicrobial peptide.

4. A composition of matter according to claim 3 wherein the peptide is a defensin peptide.

5. The composition of matter of claim 1 wherein the biologically-active compound is a drug.

6. The composition of matter of claim 5 wherein the drug is an antiviral drug or an antimicrobial drug.

7. The composition of matter of claim 1 wherein the biologically-active compound is a toxin.

8. A composition of matter according to claim 1 wherein the organic coating material is chemically degraded inside a mammalian phagocytic cell infected with a microorganism.

9. A composition of matter according to claim 1 wherein the organic coating material is a substrate for a protein having an enzymatic activity, said protein being specifically produced in a mammalian cell infected with a microorganism.

10. The composition of matter of claim 7 wherein the organic coating material is a substrate for a protein produced by the infected mammalian cell.

11. The composition of matter of claim 9 wherein the organic coating material is a substrate for a protein produced by the microorganism infecting the infected mammalian cell.

12. The composition of matter of claim 1 optionally comprising a polar lipid targeting moiety comprised of one or a plurality of polar lipid molecules, wherein the polar lipid moiety is covalently linked to the biologically-active compound.

13. The composition of matter of claim 12 wherein the polar lipid moiety is linked to the biologically-active compound through an organic spacer moiety comprising a first functional linker group and a second functional linker group.

14. The composition of matter of claim 13 wherein the organic spacer moiety allows the biologically-active compound to act without being released from the polar lipid moiety at an intracellular site.

15. A composition of matter according to claim 13 wherein the organic spacer moiety allows the facilitated hydrolytic release of the biologically-active compound at an intracellular site.

16. A composition of matter according to claim 13 wherein the organic spacer moiety allows the facilitated enzymatic release of the biologically-active compound at an intracellular site.

17. A composition of matter according to claim 13 wherein the polar lipid is acyl carnitine, acylated carnitine, sphingosine, ceramide, phosphatidyl choline, phosphatidyl glycerol, phosphatidyl ethanolamine, phosphatidyl inositol, phosphatidyl serine, cardiolipin and phosphatidic acid.

18. A pharmaceutical composition comprising the composition of matter of claim 1 in a pharmaceutically acceptable carrier.

19. A method of killing a microorganism infecting a mammalian cell, the method comprising contacting said cell with a cytotoxic amount of the composition of claim 4.

20. A method of killing a microorganism infecting a mammalian cell, the method comprising contacting said cell with a cytotoxic amount of the composition of claim 3.

21. A method of killing a microorganism infecting a mammalian cell, the method comprising contacting said cell with a cytotoxic amount of the composition of claim 4.

22. A method for treating a microbial infection in a human wherein the infecting microbe is present inside a phagocytic cell in the human, the method comprising administering a therapeutically effective amount of the composition of claim 3 to the human in a pharmaceutically acceptable carrier.

23. A method for treating a microbial infection in a human wherein the infecting microbe is present inside a phagocytic cell in the human, the method comprising administering a therapeutically effective amount of the composition of claim 6 to the human in a pharmaceutically acceptable carrier.

24. A pharmaceutical composition comprising the composition of matter of claim 13 in a pharmaceutically acceptable carrier.

25. A composition of matter according to claim 13 wherein the organic spacer moiety is a peptide of formula (amino acid)$_n$, wherein n is an integer between 2 and 100 and the peptide comprises a polymer of one or more amino acids.

* * * * *